United States Patent [19]
Gruss et al.

[11] Patent Number: 5,919,678
[45] Date of Patent: Jul. 6, 1999

[54] METHODS FOR USING A TEMPERATURE-SENSITIVE PLASMID

[75] Inventors: Alexandra Gruss, Paris; Emmanuelle Maguin, Montrouge, both of France

[73] Assignee: Institut National de la Recherche Agronomique, Paris, France

[21] Appl. No.: 08/992,334

[22] Filed: Dec. 17, 1997

Related U.S. Application Data

[62] Division of application No. 08/302,752, Dec. 27, 1994, which is a continuation of application No. PCT/FR93/00248, Mar. 12, 1993.

[30] Foreign Application Priority Data

Mar. 13, 1992 [FR] France ................................. 92 03034

[51] Int. Cl.$^6$ ........................... C12N 15/63; C12N 15/70; C12N 15/74; C12N 1/21
[52] U.S. Cl. .................. 435/172.3; 435/69.1; 435/252.3; 435/252.31; 435/252.33; 435/320.1
[58] Field of Search .............................. 435/320.1, 172.3, 435/252.3, 252.31, 252.33, 69.1, 71.1; 536/23.1, 24.1; 935/22, 33, 38, 43, 66, 72, 73, 74

[56] References Cited

U.S. PATENT DOCUMENTS 4,711,845  12/1987  Gelfand et al. ......................... 435/69.1

FOREIGN PATENT DOCUMENTS

| | | |
|---|---|---|
| 0182562 | 5/1986 | European Pat. Off. . |
| 0243856 | 11/1987 | European Pat. Off. . |
| 0334282 | 9/1989 | European Pat. Off. . |
| 0445385 | 9/1991 | European Pat. Off. . |

OTHER PUBLICATIONS

Applied and Environmental Microbiology; vol. 57, No. 2, 1991, Washington DC, pp. 539–548. Feiertag J M; Petzel J P; Pasalodos E; Baldwin K A; McKay L L "Thermosensitive Plasmid Replication Temperature–Sensitive Host Growth and Chromosomal Plasmid Integration Conferred by Lactococcus–Lactis–SSP–Cremoris Lactose Plasmids in Lactococcus–Lactis–SSP–Lactis" see the whole document. Relevant to Claims 1–4, 19–24.

Journal of Bacteriology; vol. 172, No. 8, 1990, Baltimore, U.S., pp. 4543–4584. Sozhammannan S; Dabert P; Moretto V; Ehrlich S D; Gruss A "Plus–Origin Mapping of Single–Stranded DNA Plasmid P–E–194 and Nick Site Homologies With Other Plasmids" cited in the application. See the whole document. Relevant to Claims 1, 2, 19–24.

Biological Abstracts; vol. 87 Philadelphia, PA, U.S., abstracts No. 047423. Alonso J C; Stiege C A; Tailor R H; Viret J–F "Functional Analysis of the DNA–TS Mutants of Bacillus–Subtilis Plasmid PUB110 Replication As A Model System"; see abstract & Mol Gen Genet 214 (3). 1988. 482–489. Relevant to Claims 1, 9–11.

Biological Abstracts; vol. 92, Philadelphia, PA, U.S., abstract No. 075453. Leenhouts K J; Kok J; Venema G "Replacement Recombination In Lactococcus–Lactis"; see abstract & J. Bacteriol 173 (15). 1991. 4794–4798. Relevant to Claims 5,8.

Biological Abstracts; vol. 88, Philadelphia, PA, U.S., abstract No. 107483. Priebe S D; Lacks S A "Region Of The Streptococcal Plasmid PMV158 Required For Conjugative Mobilization"; see abstract & J. Bacteriol 171 (9). 1989. 4778–4784. Relevant to Claim 15.

Journal of Bacteriology; vol. 174, No. 17, 1992, Baltimore U.S., pp. 5633–5638. Maguin E; Duwat P; Hege T; Ehrlich D; Gruss A "New Thermosensitive Plasmid For A Gram–Positive Bacteria"; see the whole document. Relevant to Claims 1–24.

Alonso et al. "Functional Analysis of the dua(Ts) Mutants of Bacillus Subtilic" Mol Gen Genet vol. 214, pp. 482–489, 1988.

Danilevich et al. "Isolation & Characterization of a Temperature–Sensitive Plasmid . . . " Mol. Biol. 18(4), 1111–1120, 1984. Abstract only.

Urlapova et al. "Temperature–Sensitive Mutants of the Plasmid RP–1" Genetuka (15) (13), 433–443, 1979. Abstract only.

Leenhouts et al. "Nucleotide Sequence & Characterization of the Broad Host Range Lactococcol Plasmid pWVO1" 26, 55–66, 1991.

*Primary Examiner*—Nancy Degen
*Attorney, Agent, or Firm*—Christie, Parker & Hale, LLP

[57] ABSTRACT

A method for the inactivation of a gene in a bacterium or for the introduction of a heterologous gene into a bacterium comprises a) introducing, by transformation or conjugation, in the bacterium a bacterial vector plasmid comprising a marker gene capable of being expressed in a bacterial host strain and an effective replication system which is temperature sensitive at and above a temperature compatible with the viability of the host strain; b) culturing the bacterium on a selective medium at a temperature below the temperature of inhibition to form a culture; c) raising the temperature of the culture to a temperature above the temperature of inhibition; and d) recovering the surviving bacteria after several multiplication cycles.

21 Claims, 21 Drawing Sheets

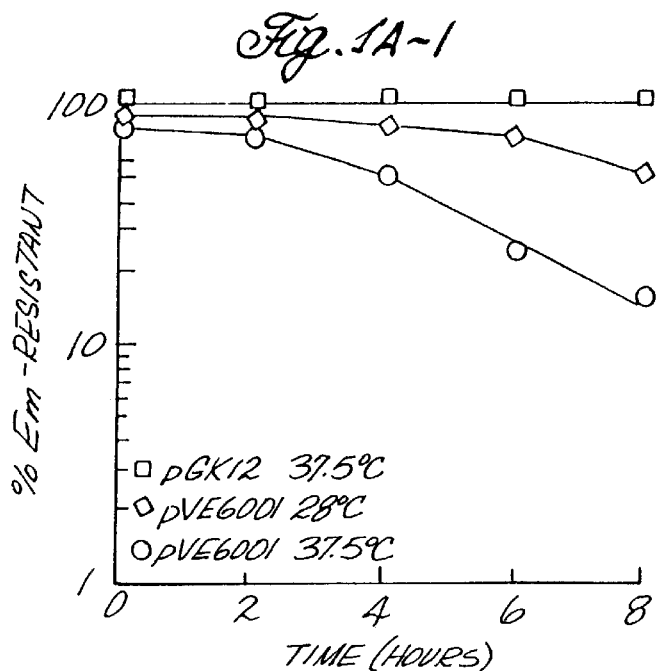 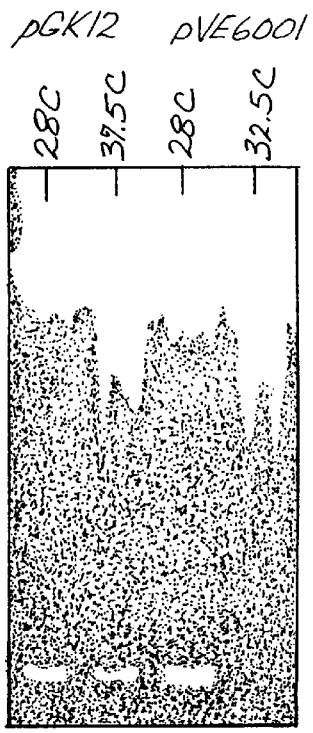
Fig. 1A-1 / Fig. 1A-2
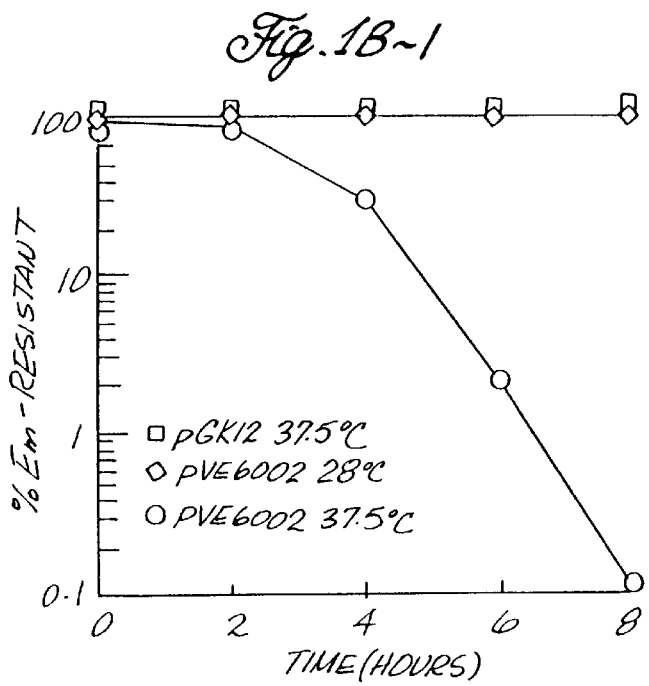 
Fig. 1B-1 / Fig. 1B-2

Fig. 5

```
                   50                  60              70        80
PE.194     LHDRDTDTEGRM........................KKEHYHILVMYEGNKSYEQI
           ***  *                               ** ***   * ***** ***
PLB.4      LHDKDVNPDGEK........................KKSHYHLVLNYKGNKSEEQI
           ***** *  *                           ** * *          ***
PHPK.255   LHDKDLNEDGSH........................KKPHFHAIIVEDKKQRPAAV
           ***** *                              ****  *             *
PADB.201   LHDKDVNPDGTI........................KKPHYHIVLAYSGPTTFNNV
           *****                                ** ***     *     *
PLS.1      LHDKDKSSIKGQKY......................KKAHYHVLYIAKNPVTADSV
           ***  *                               ** *** *   * **  **
PWV.01     LHDMDEKLDKDTWNSSDVIRNGKH.YKKPHYHVIYLARNPVTIESV
           ***** *   ** *********** *************  *****
PHS.71     LHDMDEKKDKDTWNSSDVIRNGKH.YKKPHYHVIYIARNPVTIESV
           *****  *  ** *********** *   *  * * *********
PFX.2      LHDMDEKKIKIHGIVVMLYEMEMHVIKNPHYHVYILHGNPVTIESV
           ******                                 * *  ********
CONSENS    LHD D    D                           KKPHYH    P T E V
                   50        60         70         80       90       100
                                                                           70
```

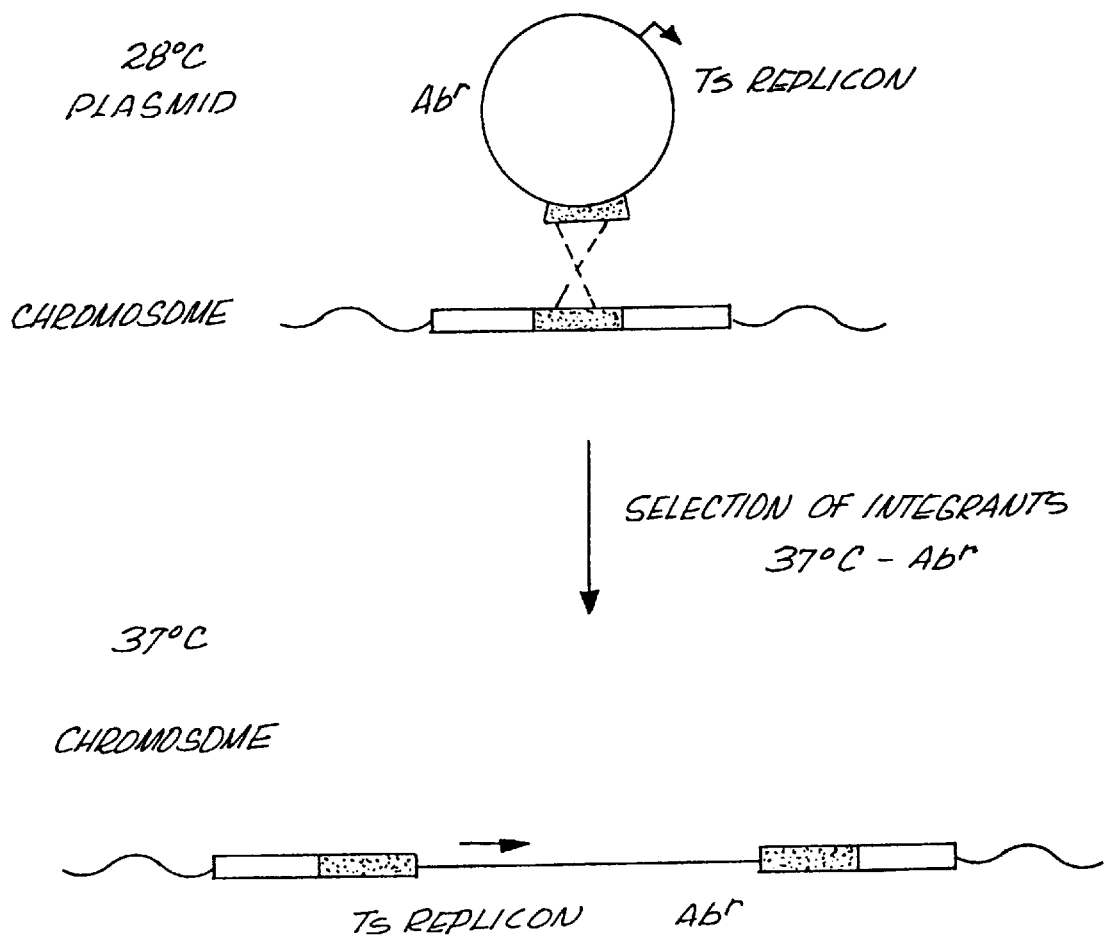

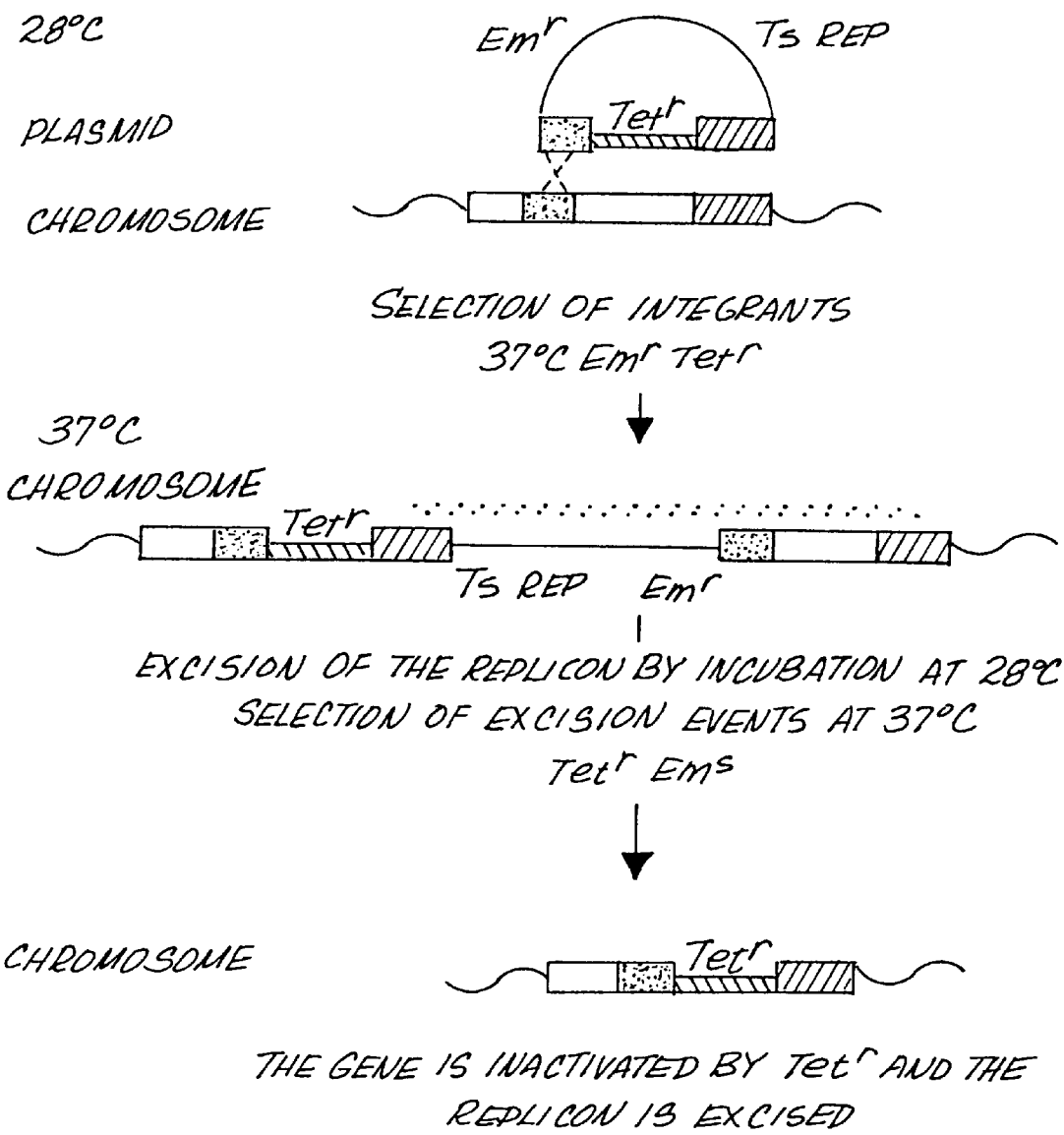

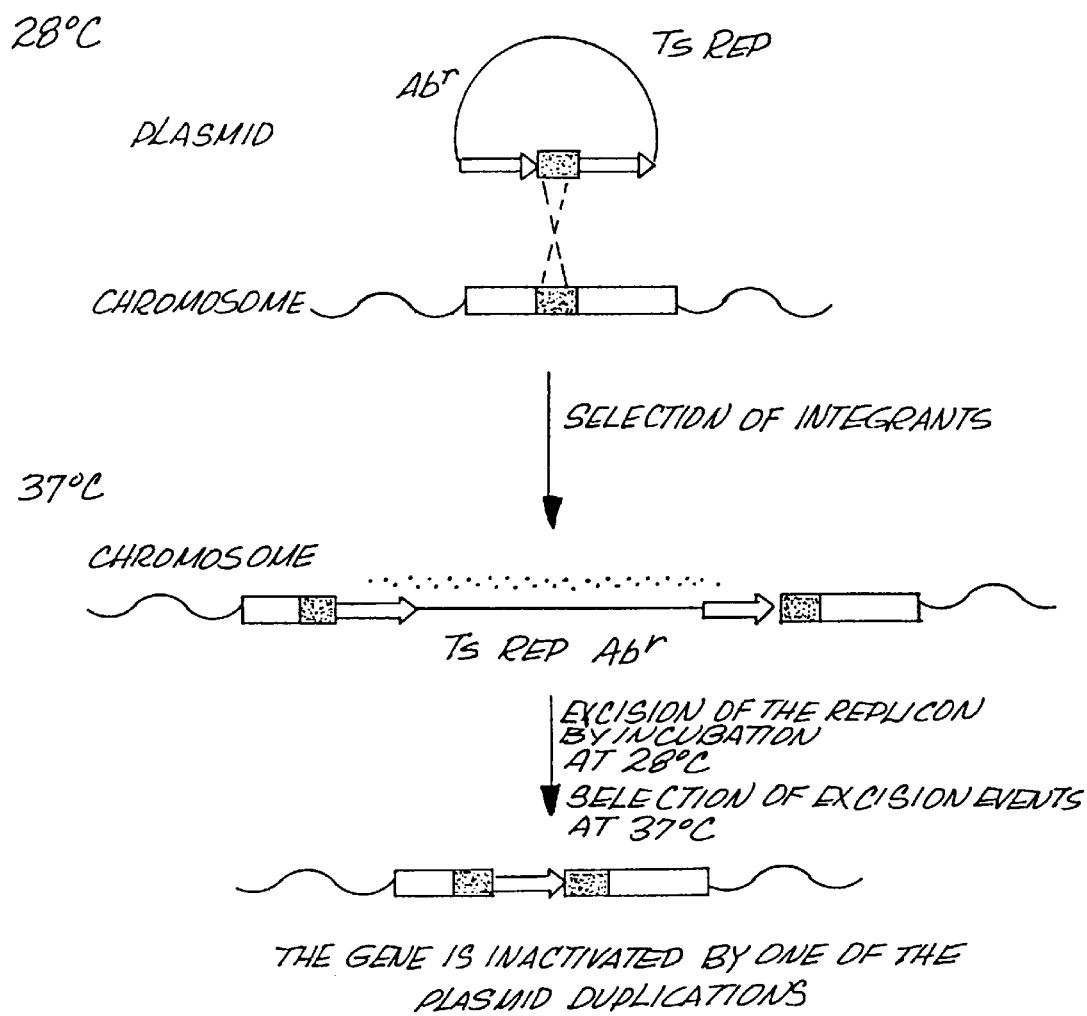

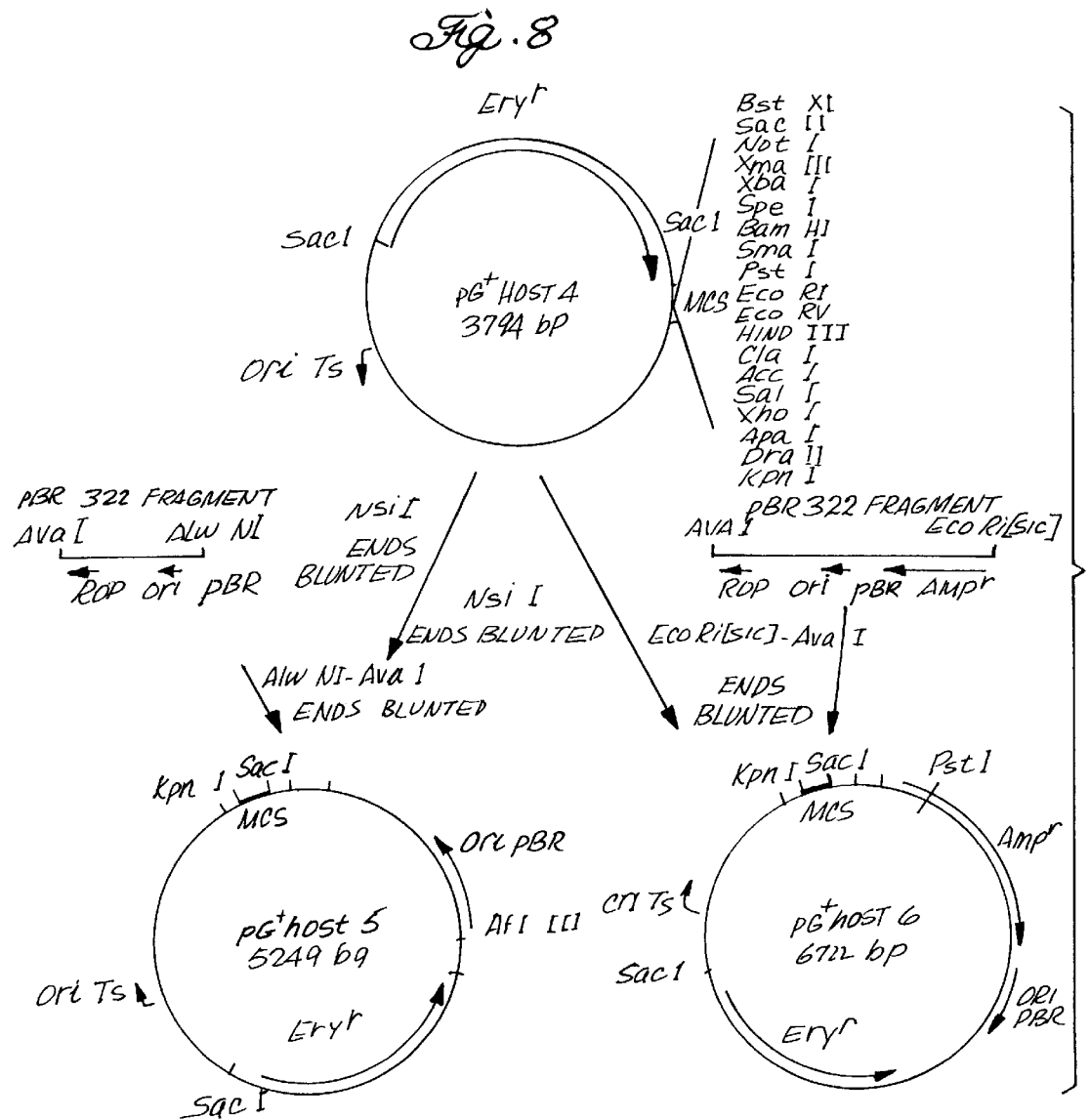

Fig. 9-1 pghost4.seq    length : 3792

```
   1  CGATTCACAA  AAAATAGGCA  CACGAAAAAC  AAGTTAAGGG  ATGCAGTTTA
  51  TGCATCCCTT  AACTTACTTA  TTAAATAATT  TATAGCTATT  GAAAAGAGAT
 101  AAGAATTGTT  CAAAGCTAAT  ATTGTTTAAA  TCGTCAATTC  CTGCATGTTT
 151  TAAGGAATTG  TTAAATTGAT  TTTTTGTAAA  TATTTCTTG   TATTCTTTGT
 201  TAACCCATTT  CATAACGAAA  TAATTATACT  TTTGTTTATC  TTTGTGTGAT
 251  ATTCTTGATT  TTTTTCTACT  TAATCTGATA  AGTGAGCTAT  TCACTTTAGG
 301  TTTAGGATGA  AAATATTCTC  TTGGAACCAT  ACTTAATATA  GAAATATCAA
 351  CTTCTGCCAT  TAAAAGTAAT  GCCAATGAGC  GTTTTGTATT  TAATAATCTT
 401  TTAGCAAACC  CGTATTCCAC  GATTAAATAA  ATCTCATTAG  CTATACTATC
 451  AAAAACAATT  TTGCGTATTA  TATCCGTACT  TATGTTATAA  GGTATATTAC
 501  CATATATTTT  ATAGGATTGG  TTTTTAGGAA  ATTTAAACTG  CAATATATCC
 551  TTGTTTAAAA  CTTGGAAATT  ATCGTGATCA  ACAAGTTTAT  TTTCTGTAGT
 601  TTTGCATAAT  TTATGGTCTA  TTTCAATGGC  AGTTACGAAA  TTACACCTCT
 651  TTACTAATTC  AAGGGTAAAA  TGGCCTTTTC  CTGAGCCGAT  TTCAAAGATA
 701  TTATCATGTT  CATTTAATCT  TATATTTGTC  ATTATTTTAT  CTATATTATG
 751  TTTTGAAGTA  ATAAAGTTTT  GACTGTGTTT  TATATTTTTC  TCGTTCATTA
 801  TAACCCTCTT  TAATTTGGTT  ATATGAATTT  TGCTTATTAA  CGATTCATTA
 851  TAACCACTTA  TTTTTTGTTT  GGTTGATAAT  GAACTGTGCT  GATTACAAAA
 901  ATACTAAAAA  TGCCCATATT  TTTTCCTCCT  TATAAAATTA  GTATAATTAT
 951  AGCACGAGCT  CTGATAAATA  TGAACATGAT  GAGTGATCGT  TAAATTTATA
1001  CTGCAATCGG  ATGCGATTAT  TGAATAAAAG  ATATGAGAGA  TTTATCTAAT
1051  TTCTTTTTTC  TTGTAAAAAA  AGAAAGTTCT  TAAAGGTTTT  ATAGTTTTGG
1101  TCGTAGAGCA  CACGGTTTAA  CGACTTAATT  ACGAAGTAAA  TAAGTCTAGT
1151  GTGTTAGACT  TTATGAAATC  TATATACGTT  TATATATATT  TATTATCGCA
1201  TTTTTTATTA  AAACGTCTCA  AAATCGTTTC  TGAGACGTTT  TAGCGTTTAT
1251  TTCGTTTAGT  TATCGGCATA  ATCGTTAAAA  CAGGCGTTAT  CGTAGCGTAA
1301  AAGCCCTTGA  GCGTAGCGTG  GCTTTGCAGC  GAAGATGTTG  TCTGTTAGAT
1351  TATGAAAGCC  GATGACTGAA  TGAAATAATA  AGCGCAGCGC  CCTTCTATTT
```

*Fig. 9~2*

| | | | | |
|---|---|---|---|---|
| 2851 ATAAATAAAA | GCCCCCTGAC | GAAAGTCGAA | GGGGGTTTTT | ATTTTGGTTT |
| 2901 GATGTTGCGA | TTAATAGCAA | TACAATTGCA | ATAAACAAAA | TGATCTTCCT |
| 2951 TCAGGTTATG | ACCATCTGTG | CCAGTTCGTA | ATGTCTGGTC | AACTTTCCGA |
| 3001 CTCTGAGAAA | CTTCTGGAAT | CGCTAGAGAA | TTTCTGGAAT | GGGATTCAGG |
| 3051 AGTGGACAGA | ACGACACGGA | TATATAGTGG | ATGTGTCAAA | ACGCATACCA |
| 3101 TTTTGAACGA | TGACCTCTAA | TAATTGTTAA | TCATGTTGGT | TACGTATTTA |
| 3151 TTAACTTCTC | CTAGTATTAG | TAATTATCAT | GGCTGTCATG | GCGCATTAAC |
| 3201 GGAATAAAGG | GTGTGCTTAA | ATCGGGCCAT | TTTGCGTAAT | AAGAAAAAGG |
| 3251 ATTAATTATG | AGCGAATTGA | ATTAATAATA | AGGTAATAGA | TTTACATTAG |
| 3301 AAAATGAAAG | GGGATTTTAT | GCGTGAGAAT | GTTACAGTCT | ATCCCTGGCG |
| 3351 AAAGGGGGAT | GTGCTGCAAG | GCGATTAAGT | TGGGTAACGC | CAGGGTTTTC |
| 3401 CCAGTCACGA | CGTTGTAAAA | CGACGGCCAG | TGAGCGCGCG | TAATACGACT |
| 3451 CACTATAGGG | CGAATTGGGT | ACCGGGCCCC | CCTCGAGGT | CGACGGTATC |
| 3501 GATAAGCTTG | ATATCGAATT | CCTGCAGCCC | GGGGGATCCA | CTAGTTCTAG |
| 3551 AGCGGCCGCC | ACCGCGGTGG | AGCTCCAGCT | TTTGTTCCCT | TTAGTGAGGG |
| 3601 TTAATTGCGC | GCTTGGCGTA | ATCATGGTCA | TAGCTGTTTC | CTGTGTGAAA |
| 3651 TTGTTATCCG | CTCACAATTC | CACACAACAT | ACGAGCCGGA | AGCATAAAGT |
| 3701 GTAAAGCCTG | GGGTGCCTAA | TGAGTGAGCT | AACTCACATT | AATTGCGTTG |
| 3751 CGCTCACTGC | CCGCTTTCCA | GTCGGGAAAC | CTGTCGTGCC | AG |

*Fig.* 9-3

| | | | | |
|---|---|---|---|---|
| 1401 CGGTTGGAGG | AGGCTCAAGG | GAGTATGAGG | GAATGAAATT | CCCTCATGGG |
| 1451 TTTGATTTTA | AAAATTGCTT | GCAATTTTGC | CGAGCGGTAG | CGCTGGAAAA |
| 1501 TTTTTGAAAA | AAATTTGGAA | TTTGGAAAAA | AATGGGGGGA | AAGGAAGCGA |
| 1551 ATTTTGCTTC | CGTACTACGA | CCCCCCATTA | AGTGCCGAGT | GCCAATTTTT |
| 1601 GTGCCAAAAA | CGCTCTATCC | CAACTGGCTC | AAGGGTTTAA | GGGGTTTTTC |
| 1651 AATCGCCAAC | GAATCGCCAA | CGTTTCGCC | AACGTTTTTT | ATAAATCTAT |
| 1701 ATTTAAGTAG | CTTTATTGTT | GTTTTTATGA | TTACAAAGTG | ATACACTAAC |
| 1751 TTTATAAAAT | TATTTGATTG | GAGTTTTTTA | AATGGTGATT | TCAGAATCGA |
| 1801 AAAAAAGAGT | TATGATTTCT | CTGACAAAAG | AGCAAGATAA | AAAATTAACA |
| 1851 GATATGGCGA | AACAAAAGG | TTTTTCAAAA | TCTGCGGTTG | CGGCGTTAGC |
| 1901 TATAGAAGAA | TATGCAAGAA | AGGAATCAGA | ACAAAAAAAA | TAAGCGAAAG |
| 1951 CTCGCGTTTT | TAGAAGGATA | CGAGTTTTCG | CTACTTGTTT | TTGATAAGGT |
| 2001 AATTATATCA | TGGCTATTAA | AAATACTAAA | GCTAGAAATT | TTGGATTTTT |
| 2051 ATTATATCCT | GACTCAATTC | CTAATGATTG | GAAAGAAAAA | TTAGAGAGTT |
| 2101 TGGGCGTATC | TATGGCTGTC | AGTCCTTTAC | ACGATATGGA | CGAAAAAAAA |
| 2151 GATAAAGATA | CATGGAATAA | TAGTAATATT | ATACAAAATG | GAAAGCACTA |
| 2201 TAAAAAACCA | CACTATCACG | TTATATATAT | TGCACGAAAT | CCTGTAACAA |
| 2251 TAGAAAGCGT | TAGGAACAAG | ATTAAGCGAA | AATTGGGGAA | TAGTTCAGTT |
| 2301 GCTCATGTTG | AGATACTTGA | TTATATCAAA | GGTTCATATG | AATATTTGAC |
| 2351 TCATGAATCA | AAGGACGCTA | TTGCTAAGAA | TAAACATATA | TACGACAAAA |
| 2401 AAGATATTTT | GAACATTAAT | GATTTTGATA | TTGACCGCTA | TATAACACTT |
| 2451 GATGAAAGCC | AAAAAAGAGA | ATTGAAGAAT | TTACTTTTAG | ATATAGTGGA |
| 2501 TGACTATAAT | TTGGTAAATA | CAAAAGATTT | AATGGCTTTT | ATTCGCCTTA |
| 2551 GGGGAGCGGA | GTTTGGAATT | TTAAATACGA | ATGATGTAAA | AGATATTGTT |
| 2601 TCAACAAACT | CTAGCGCCTT | TAGATTATGG | TTTGAGGGCA | ATTATCAGTG |
| 2651 TGGATATAGA | GCAAGTTATG | CAAAGGTTCT | TGATGCTGAA | ACGGGGGAAA |
| 2701 TAAAATGACA | AACAAAGAAA | AAGAGTTATT | TGCTGAAAAT | GAGGAATTAA |
| 2751 AAAAAGAAAT | TAAGGACTTA | AAAGAGCGTA | TTGAAAGATA | CAGAGAAATG |
| 2801 GAAGTTGAAT | TAAGTACAAC | AATAGATTTA | TTGAGAGGAG | GGATTATTGA |

Fig. 10-1 pghost5.seq   length : 5284

Length: 5234

```
    1 AGGCACACGA AAAACAAGTT AAGGGATGCA GTTTA
                                              >seqed
      (included) of: pbr322.seq check: 5483 from: 1426
      to 2886>                        TCGGG CAGCGTTGGG
   51 TCCTGGCCAC GGGTGCGCAT GATCGTGCTC CTGTCGTTGA GGACCCGGCT
  101 AGGCTGGCGG GGTTGCCTTA CTGGTTAGCA GAATGAATCA CCGATACGCG
  151 AGCGAACGTG AAGCGACTGC TGCTGCAAAA CGTCTGCGAC CTGAGCAACA
  201 ACATGAATGG TCTTCGGTTT CCGTGTTTCG TAAAGTCTGG AAACGCGGAA
  251 GTCAGCGCCC TGCACCATTA TGTTCCGGAT CTGCATCGCA GGATGCTGCT
  301 GGCTACCCTG TGGAACACCT ACATCTGTAT TAACGAAGCG CTGGCATTGA
  351 CCCTGAGTGA TTTTTCTCTG GTCCGCCGC ATCCATACCG CCAGTTGTTT
  401 ACCCTCACAA CGTTCCAGTA ACCGGGCATG TTCATCATCA GTAACCCGTA
  451 TCGTGAGCAT CCTCTCTCGT TTCATCGGTA TCATTACCCC CATGAACAGA
  501 AATCCCCCTT ACACGGAGGC ATCAGTGACC AAACAGGAAA AAACCGCCCT
  551 TAACATGGCC CGCTTTATCA GAAGCCAGAC ATTAACGCTT CTGGAGAAAC
  601 TCAACGAGCT GGACGCGGAT GAACAGGCAG ACATCTGTGA ATCGCTTCAC
  651 GACCACGCTG ATGAGCTTTA CCGCAGCTGC CTCGCGCGTT TCGGTGATGA
  701 CGGTGAAAAC CTCTGACACA TGCAGCTCCC GGAGACGGTC ACAGCTTGTC
  751 TGTAAGCGGA TGCCGGGAGC AGACAAGCCC GTCAGGGCGC GTCAGCGGGT
  801 GTTGGCGGGT GTCGGGCGC AGCCATGACC CAGTCACGTA GCGATAGCGG
  851 AGTGTATACT GGCTTAACTA TGCGGCATCA GAGCAGATTG TACTGAGAGT
  901 GCACCATATG CGGTGTGAAA TACCGCACAG ATGCGTAAGG AGAAAATACC
  951 GCATCAGGCG CTCTTCCGCT TCCTCGCTCA CTGACTCGCT GCGCTCGGTC
 1001 GTTCGGCTGC GGCGAGCGGT ATCAGCTCAC TCAAAGGCGG TAATACGGTT
 1051 ATCCACAGAA TCAGGGGATA ACGCAGGAAA GAACATGTGA GCAAAAGGCC
 1101 AGCAAAAGGC CAGGAACCGT AAAAAGGCCG CGTTGCTGGC GTTTTTCCAT
 1151 AGGCTCCGCC CCCCTGACGA GCATCACAAA AATCGACGCT CAAGTCAGAG
 1201 GTGGCGAAAC CCGACAGGAC TATAAAGATA CCAGGCGTTT CCCCCTGGAA
```

Fig. 10-2

```
1251 GCTCCCTCGT GCGCTCTCCT GTTCCGACCC TGCCGCTTAC CGGATACCTG
1301 TCCGCCTTTC TCCCTTCGGG AAGCGTGGCG CTTTCTCATA GCTCACGCTG
1351 TAGGTATCTC AGTTCGGTGT AGGTCGTTCG CTCCAAGCTG GGCTGTGTGC
1401 ACGAACCCCC CGTTCAGCCC GACCGCTGCG CCTTATCCGG TAACTATCGT
1451 CTTGAGTCCA ACCCGGTAAG ACACGACTTA TCGCCACTGG CAGCAG <seq
``` ed (included) of: pbr322.seq check: 5483 from: 1426
to: 2886>
                                                                                               TCCC

```
1501 TTAACTTACT TATTAAATAA TTTATAGCTA TTGAAAAGAG ATAAGAATTG
1551 TTCAAAGCTA ATATTGTTTA AATCGTCAAT TCCTGCATGT TTTAAGGAAT
1601 TGTTAAATTG ATTTTTTGTA AATATTTTCT TGTATTCTTT GTTAACCCAT
1651 TTCATAACGA AATAATTATA CTTTTGTTTA TCTTTGTGTG ATATTCTTGA
1701 TTTTTTTCTA CTTAATCTGA TAAGTGAGCT ATTCACTTTA GGTTTAGGAT
1751 GAAAATATTC TCTTGGAACC ATACTTAATA TAGAAATATC AACTTCTGCC
1801 ATTAAAGTA ATGCCAATGA GCGTTTTGTA TTTAATAATC TTTTAGCAAA
1851 CCCGTATTCC ACGATTAAAT AAATCTCATT AGCTATACTA TCAAAACAA
1901 TTTTGCGTAT TATATCCGTA CTTATGTTAT AAGGTATATT ACCATATATT
1951 TTATAGGATT GGTTTTTAGG AAATTTAAAC TGCAATATAT CCTTGTTTAA
2001 AACTTGGAAA TTATCGTGAT CAACAAGTTT ATTTTCTGTA GTTTTGCATA
2051 ATTTATGGTC TATTTCAATG GCAGTTACGA AATTACACCT CTTTACTAAT
2101 TCAAGGGTAA AATGGCCTTT TCCTGAGCCG ATTTCAAAGA TATTATCATG
2151 TTCATTTAAT CTTATATTTG TCATTATTTT ATCTATATTA TGTTTTGAAG
2201 TAATAAAGTT TTGACTGTGT TTTATATTTT TCTCGTTCAT TATAACCCTC
2251 TTTAATTTGG TTATATGAAT TTTGCTTATT AACGATTCAT TATAACCACT
2301 TATTTTTTGT TTGGTTGATA ATGAACTGTG CTGATTACAA AAATACTAAA
2351 AATGCCCATA TTTTTTCCTC CTTATAAAAT TAGTATAATT ATAGCACGAG
2401 CTCTGATAAA TATGAACATG ATGAGTGATC GTTAAATTTA TACTGCAATC
2451 GGATGCGATT ATTGAATAAA AGATATGAGA GATTTATCTA ATTTCTTTTT
2501 TCTTGTAAAA AAAGAAAGTT CTTAAAGGTT TTATAGTTTT GGTCGTAGAG
2551 CACACGGTTT AACGACTTAA TTACGAAGTA AATAAGTCTA GTGTGTTAGA
```

Fig. 10-3

```
2601  CTTTATGAAA  TCTATATACG  TTTATATATA  TTTATTATC
                                                    >SEQED
      (included) of: pwv01. check: 7166 from: 1 to: 1744>
                                                   C GATTTTTTAT
2651  TAAAACGTCT  CAAAATCGTT  TCTGAGACGT  TTTAGCGTTT  ATTTCGTTTA
2701  GTTATCGGCA  TAATCGTTAA  AACAGGCGTT  ATCGTAGCGT  AAAAGCCCTT
2751  GAGCGTAGCG  TGGCTTTGCA  GCGAAGATGT  TGTCTGTTAG  ATTATGAAAG
2801  CCGATGACTG  AATGAAATAA  TAAGCGCAGC  GCCCTTCTAT  TTCGGTTGGA
2851  GGAGGCTCAA  GGGAGTATGA  GGGAATGAAA  TTCCCTCATG  GGTTTGATTT
2901  TAAAAATTGC  TTGCAATTTT  GCCGAGCGGT  AGCGCTGGAA  AATTTTTGAA
2951  AAAAATTTGG  AATTTGGAAA  AAAATGGGGG  GAAAGGAAGC  GAATTTTGCT
3001  TCCGTACTAC  GACCCCCCAT  TAAGTGCCGA  GTGCCAATTT  TTGTGCCAAA
3051  AACGCTCTAT  CCCAACTGGC  TCAAGGGTTT  AAGGGGTTTT  TCAATCGCCA
3101  ACGAATCGCC  AACGTTTTCG  CCAACGTTTT  TTATAAATCT  ATATTTAAGT
3151  AGCTTTATTG  TTGTTTTTAT  GATTACAAAG  TGATACACTA  ACTTTATAAA
3201  ATTATTTGAT  TGGAGTTTTT  TAAATGGTGA  TTTCAGAATC  GAAAAAAGA
3251  GTTATGATTT  CTCTGACAAA  AGAGCAAGAT  AAAAAATTAA  CAGATATGGC
3301  GAAACAAAAA  GGTTTTTCAA  AATCTGCGGT  TGCGGCGTTA  GCTATAGAAG
3351  AATATGCAAG  AAAGGAATCA  GAACAAAAAA  AATAAGCGAA  AGCTCGCGTT
3401  TTTAGAAGGA  TACGAGTTTT  CGCTACTTGT  TTTTGATAAG  GTAATTATAT
3451  CATGGCTATT  AAAAATACTA  AAGCTAGAAA  TTTTGGATTT  TTATTATATC
3501  CTGACTCAAT  TCCTAATGAT  TGGAAAGAAA  AATTAGAGAG  TTTGGGCGTA
3551  TCTATGGCTG  TCAGTCCTTT  ACACGATATG  GACGAAAAAA  AAGATAAAGA
3601  TACATGGAAT  AATAGTAATA  TTATACAAAA  TGGAAAGCAC  TATAAAAAAC
3651  CACACTATCA  CGTTATATAT  ATTGCACGAA  ATCCTGTAAC  AATAGAAAGC
3701  GTTAGGAACA  AGATTAAGCG  AAAATTGGGG  AATAGTTCAG  TTGCTCATGT
3751  TGAGATACTT  GATTATATCA  AAGGTTCATA  TGAATATTTG  ACTCATGAAT
3801  CAAAGGACGC  TATTGCTAAG  AATAAACATA  TATACGACAA  AAAAGATATT
3851  TTGAACATTA  ATGATTTTGA  TATTGACCGC  TATATAACAC  TTGATGAAAG
3901  CCAAAAAAGA  GAATTGAAGA  ATTTACTTTT  AGATATAGTG  GATGACTATA
3951  ATTTGGTAAA  TACAAAAGAT  TTAATGGCTT  TTATTCGCCT  TAGGGGAGCG
```

Fig. 10-4

```
4001  GAGTTTGGAA  TTTTAAATAC  GAATGATGTA  AAAGATATTG  TTTCAACAAA
4051  CTCTAGCGCC  TTTAGATTAT  GGTTTGAGGG  CAATTATCAG  TGTGGATATA
4101  GAGCAAGTTA  TGCAAAGGTT  CTTGATGCTG  AAACGGGGA   AATAAAATGA
4151  CAAACAAAGA  AAAAGAGTTA  TTTGCTGAAA  ATGAGGAATT  AAAAAAAGAA
4201  ATTAAGGACT  TAAAAGAGCG  TATTGAAAGA  TACAGAGAAA  TGGAAGTTGA
4251  ATTAAGTACA  ACAATAGATT  TATTGAGAGG  AGGGATTATT  GAATAAATAA
4301  AAGCCCCTG   ACGAAAGTCG  AAGGGGGTTT  TTATTTTGGT  TTGATGTTGC
4351  GATTAATAGC  AATACAATTG  CAATAAACAA  AAT
```
<SEQED (included) of: pwv01. check: 7166 from: 1 to: 1744<
>SEQED (included) reverse of: pub110. seq check: 5091 from: 1964 to: 2366>

```
                                            GATCTTC     CTTCAGGTTA
4401  TGACCATCTG  TGCCAGTTCG  TAATGTCTGG  TCAACTTTCC  GACTCTGAGA
4451  AACTTCTGGA  ATCGCTAGAG  AATTTCTGGA  ATGGGATTCA  GGAGTGGACA
4501  GAACGACACG  GATATATAGT  GGATGTGTCA  AAACGCATAC  CATTTTGAAC
4551  GATGACCTCT  AATAATTGTT  AATCATGTTG  GTTACGTATT  TATTAACTTC
4601  TCCTAGTATT  AGTAATTATC  ATGGCTGTCA  TGGCGCATTA  ACGGAATAAA
4651  GGGTGTGCTT  AAATCGGGCC  ATTTTGCGTA  ATAAGAAAAA  GGATTAATTA
4701  TGAGCGAATT  GAATTAATAA  TAAGGTAATA  GATTTACATT  AGAAAATGAA
4751  AGGGGATTTT  ATGCGTGAGA  ATGTTACAGT  CTATCC
                                              <SEQED
```
(included) reverse of: pub110. seq check: 5091 from: 1964 to: 2366<
(included) of: pak. seq check: 8495 from: 530
>seqed
to: 977>

```
                                             CTGG        CGAAAGGGGG
4801  ATGTGCTGCA  AGGCGATTAA  GTTGGGTAAC  GCCAGGGTTT  TCCCAGTCAC
4851  GACGTTGTAA  AACGACGGCC  AGTGAGCGCG  CGTAATACGA  CTCACTATAG
4901  GGCGAATTGG  GTACCGGGCC  CCCCCTCGAG  GTCGACGGTA  TCGATAAGCT
4951  TGATATCGAA  TTCCTGCAGC  CCGGGGATC   CACTAGTTCT  AGAGCGGCCG
5001  CCACCGCGGT  GGAGCTCCAG  CTTTTGTTCC  CTTTAGTGAG  GGTTAATTGC
5051  GCGCTTGGCG  TAATCATGGT  CATAGCTGTT  TCCTGTGTGA  AATTGTTATC
5101  CGCTCACAAT  TCCACACAAC  ATACGAGCCG  GAAGCATAAA  GTGTAAAGCC
```

*Fig. 10-5*

```
5151  TGGGGTGCCT  AATGAGTGAG  CTAACTCACA  TTAATTGCGT  TGCGCTCACT
5201  GCCCGCTTTC  CAGTCGGGAA  ACCTGTCGTG  CCAG
                                              <seqed (included)
     of: psk. seq check: 8495 from: 530 to: 977<
                                         >SEQED (included)
     of: pcl.ba check: 2015 from: 974 to: 2004>
```

Fig. 11-1 pghost6.seq          length 6722       Type: N

```
   1  CGATTCACAA  AAAATAGGCA  CACGAAAAAC  AAGTTAAGGG  ATGCAGTTTA
  51  AATTCTTGAA  GACGAAAGGG  CCTCGTGATA  CGCCTATTTT  TATAGGTTAA
 101  TGTCATGATA  ATAATGGTTT  CTTAGACGTC  AGGTGGCACT  TTTCGGGGAA
 151  ATGTGCGCGG  AACCCTATT   TGTTTATTTT  TCTAAATACA  TTCAAATATG
 201  TATCCGCTCA  TGAGACAATA  ACCCTGATAA  ATGCTTCAAT  AATATTGAAA
 251  AAGGAAGAGT  ATGAGTATTC  AACATTTCCG  TGTCGCCCTT  ATTCCCTTTT
 301  TTGCGGCATT  TTGCCTTCCT  GTTTTTGCTC  ACCCAGAAAC  GCTGGTGAAA
 351  GTAAAAGATG  CTGAAGATCA  GTTGGGTGCA  CGAGTGGGTT  ACATCGAACT
 401  GGATCTCAAC  AGCGGTAAGA  TCCTTGAGAG  TTTTCGCCCC  GAAGAACGTT
 451  TTCCAATGAT  GAGCACTTTT  AAAGTTCTGC  TATGTGGCGC  GGTATTATCC
 501  CGTGTTGACG  CCGGGCAAGA  GCAACTCGGT  CGCCGCATAC  ACTATTCTCA
 551  GAATGACTTG  GTTGAGTACT  CACCAGTCAC  AGAAAAGCAT  CTTACGGATG
 601  GCATGACAGT  AAGAGAATTA  TGCAGTGCTG  CCATAACCAT  GAGTGATAAC
 651  ACTGCGGCCA  ACTTACTTCT  GACAACGATC  GGAGGACCGA  AGGAGCTAAC
 701  CGCTTTTTTG  CACAACATGG  GGGATCATGT  AACTCGCCTT  GATCGTTGGG
 751  AACCGGAGCT  GAATGAAGCC  ATACCAAACG  ACGAGCGTGA  CACCACGATG
 801  CCTGCAGCAA  TGGCAACAAC  GTTGCGCAAA  CTATTAACTG  GCGAACTACT
 851  TACTCTAGCT  TCCCGGCAAC  AATTAATAGA  CTGGATGGAG  GCGGATAAAG
 901  TTGCAGGACC  ACTTCTGCGC  TCGGCCCTTC  CGGCTGGCTG  GTTTATTGCT
 951  GATAAATCTG  GAGCCGGTGA  GCGTGGGTCT  CGCGGTATCA  TTGCAGCACT
1001  GGGGCCAGAT  GGTAAGCCCT  CCCGTATCGT  AGTTATCTAC  ACGACGGGGA
1051  GTCAGGCAAC  TATGGATGAA  CGAAATAGAC  AGATCGCTGA  GATAGGTGCC
1101  TCACTGATTA  AGCATTGGTA  ACTGTCAGAC  CAAGTTTACT  CATATATACT
1151  TTAGATTGAT  TTAAAACTTC  ATTTTTAATT  TAAAAGGATC  TAGGTGAAGA
1201  TCCTTTTTGA  TAATCTCATG  ACCAAAATCC  CTTAACGTGA  GTTTTCGTTC
1251  CACTGAGCGT  CAGACCCCGT  AGAAAGATC   AAAGGATCTT  CTTGAGATCC
1301  TTTTTTTCTG  CGCGTAATCT  GCTGCTTGCA  AACAAAAAAA  CCACCGCTAC
1351  CAGCGGTGGT  TTGTTTGCCG  GATCAAGAGC  TACCAACTCT  TTTTCCGAAG
```

Fig. 11-2

```
1401  GTAACTGGCT  TCAGCAGAGC  GCAGATACCA  AATACTGTCC  TTCTAGTGTA
1451  GCCGTAGTTA  GGCCACCACT  TCAAGAACTC  TGTAGCACCG  CCTACATACC
1501  TCGCTCTGCT  AATCCTGTTA  CCAGTGGCTG  CTGCCAGTGG  CGATAAGTCG
1551  TGTCTTACCG  GGTTGGACTC  AAGACGATAG  TTACCGGATA  AGGCGCAGCG
1601  GTCGGGCTGA  ACGGGGGGTT  CGTGCACACA  GCCCAGCTTG  GAGCGAACGA
1651  CCTACACCGA  ACTGAGATAC  CTACAGCGTG  AGCTATGAGA  AAGCGCCACG
1701  CTTCCCGAAG  GGAGAAAGGC  GGACAGGTAT  CCGGTAAGCG  GCAGGGTCGG
1751  AACAGGAGAG  CGCACGAGGG  AGCTTCCAGG  GGGAAACGCC  TGGTATCTTT
1801  ATAGTCCTGT  CGGGTTTCGC  CACCTCTGAC  TTGAGCGTCG  ATTTTTGTGA
1851  TGCTCGTCAG  GGGGGCGGAG  CCTATGGAAA  AACGCCAGCA  ACGCGGCCTT
1901  TTTACGGTTC  CTGGCCTTTT  GCTGGCCTTT  TGCTCACATG  TTCTTTCCTG
1951  CGTTATCCCC  TGATTCTGTG  GATAACCGTA  TTACCGCCTT  TGAGTGAGCT
2001  GATACCGCTC  GCCGCAGCCG  AACGACCGAG  CGCAGCGAGT  CAGTGAGCGA
2051  GGAAGCGGAA  GAGCGCCTGA  TGCGGTATTT  TCTCCTTACG  CATCTGTGCG
2101  GTATTTCACA  CCGCATATGG  TGCACTCTCA  GTACAATCTG  CTCTGATGCC
2151  GCATAGTTAA  GCCAGTATAC  ACTCCGCTAT  CGCTACGTGA  CTGGGTCATG
2201  GCTGCGCCCC  GACACCCGCC  AACACCCGCT  GACGCGCCCT  GACGGGCTTG
2251  TCTGCTCCCG  GCATCCGCTT  ACAGACAAGC  TGTGACCGTC  TCCGGGAGCT
2301  GCATGTGTCA  GAGGTTTTCA  CCGTCATCAC  CGAAACGCGC  GAGGCAGCTG
2351  CGGTAAAGCT  CATCAGCGTG  GTCGTGAAGC  GATTCACAGA  TGTCTGCCTG
2401  TTCATCCGCG  TCCAGCTCGT  TGAGTTTCTC  CAGAAGCGTT  AATGTCTGGC
2451  TTCTGATAAA  GCGGGCCATG  TTAAGGGCGG  TTTTTTCCTG  TTTGGTCACT
2501  GATGCCTCCG  TGTAAGGGGG  ATTTCTGTTC  ATGGGGGTAA  TGATACCGAT
2551  GAAACGAGAG  AGGATGCTCA  CGATACGGGT  TACTGATGAT  GAACATGCCC
2601  GGTTACTGGA  ACGTTGTGAG  GGTAAACAAC  TGGCGGTATG  GATGCGGCGG
2651  GACCAGAGAA  AAATCACTCA  GGGTCAATGC  CAGCGCTTCG  TTAATACAGA
2701  TGTAGGTGTT  CCACAGGGTA  GCCAGCAGCA  TCCTGCGATG  CAGATCCGGA
2751  ACATAATGGT  GCAGGGCGCT  GACTTCCGCG  TTTCCAGACT  TTACGAAACA
2801  CGGAAACCGA  AGACCATTCA  TGTTGTTGCT  CAGGTCGCAG  ACGTTTTGCA
```

Fig. 11-3

```
2851  GCAGCAGTCG  CTTCACGTTC  GCTCGCGTAT  CGGTGATTCA  TTCTGCTAAC
2901  CAGTAAGGCA  ACCCCGCCAG  CCTAGCCGGG  TCCTCAACGA  CAGGAGCACG
2951  ATCATGCGCA  CCCGTGGCCA  GGACCCAACG  CTGCTCCCTT  AACTTACTTA
3001  TTAAATAATT  TATAGCTATT  GAAAAGAGAT  AAGAATTGTT  CAAAGCTAAT
3051  ATTGTTTAAA  TCGTCAATTC  CTGCATGTTT  TAAGGAATTG  TTAAATTGAT
3101  TTTTTGTAAA  TATTTTCTTG  TATTCTTTGT  TAACCCATTT  CATAACGAAA
3151  TAATTATACT  TTTGTTTATC  TTTGTGTGAT  ATTCTTGATT  TTTTTCTACT
3201  TAATCTGATA  AGTGAGCTAT  TCACTTTAGG  TTTAGGATGA  AAATATTCTC
3251  TTGGAACCAT  ACTTAATATA  GAAATATCAA  CTTCTGCCAT  TAAAAGTAAT
3301  GCCAATGAGC  GTTTTGTATT  TAATAATCTT  TTAGCAAACC  CGTATTCCAC
3351  GATTAAATAA  ATCTCATTAG  CTATACTATC  AAAACAATT   TTGCGTATTA
3401  TATCCGTACT  TATGTTATAA  GGTATATTAC  CATATATTTT  ATAGGATTGG
3451  TTTTTAGGAA  ATTTAAACTG  CAATATATCC  TTGTTTAAAA  CTTGGAAATT
3501  ATCGTGATCA  ACAAGTTTAT  TTTCTGTAGT  TTTGCATAAT  TTATGGTCTA
3551  TTTCAATGGC  AGTTACGAAA  TTACACCTCT  TTACTAATTC  AAGGGTAAAA
3601  TGGCCTTTTC  CTGAGCCGAT  TTCAAAGATA  TTATCATGTT  CATTTAATCT
3651  TATATTTGTC  ATTATTTAT   CTATATTATG  TTTTGAAGTA  ATAAAGTTTT
3701  GACTGTGTTT  TATATTTTTC  TCGTTCATTA  TAACCCTCTT  TAATTTGGTT
3751  ATATGAATTT  TGCTTATTAA  CGATTCATTA  TAACCACTTA  TTTTTTGTTT
3801  GGTTGATAAT  GAACTGTGCT  GATTACAAAA  ATACTAAAAA  TGCCCATATT
3851  TTTTCCTCCT  TATAAAATTA  GTATAATTAT  AGCACGAGCT  CTGATAAATA
3901  TGAACATGAT  GAGTGATCGT  TAAATTTATA  CTGCAATCGG  ATGCGATTAT
3951  TGAATAAAAG  ATATGAGAGA  TTTATCTAAT  TTCTTTTTTC  TTGTAAAAAA
4001  AGAAAGTTCT  TAAGGTTTT   ATAGTTTTGG  TCGTAGAGCA  CACGGTTTAA
4051  CGACTTAATT  ACGAAGTAAA  TAAGTCTAGT  GTGTTAGACT  TTATGAAATC
4101  TATATACGTT  TATATATATT  TATTATCCGA  TTTTTTATTA  AAACGTCTCA
4151  AAATCGTTTC  TGAGACGTTT  TAGCGTTTAT  TTCGTTTAGT  TATCGGCATA
4201  ATCGTTAAAA  CAGGCGTTAT  CGTAGCGTAA  AAGCCCTTGA  GCGTAGCGTG
4251  GCTTTGCAGC  GAAGATGTTG  TCTGTTAGAT  TATGAAAGCC  GATGACTGAA
```

Fig. 11-4

| | | | | | |
|---|---|---|---|---|---|
| 4301 | TGAAATAATA | AGCGCAGCGC | CCTTCTATTT | CGGTTGGAGG | AGGCTCAAGG |
| 4351 | GAGTATGAGG | GAATGAAATT | CCCTCATGGG | TTTGATTTTA | AAAATTGCTT |
| 4401 | GCAATTTTGC | CGAGCGGTAG | CGCTGGAAAA | TTTTTGAAAA | AAATTTGGAA |
| 4451 | TTTGGAAAAA | AATGGGGGGA | AAGGAAGCGA | ATTTTGCTTC | CGTACTACGA |
| 4501 | CCCCCCATTA | AGTGCCGAGT | GCCAATTTTT | GTGCCAAAAA | CGCTCTATCC |
| 4551 | CAACTGGCTC | AAGGGTTTAA | GGGGTTTTTC | AATCGCCAAC | GAATCGCCAA |
| 4601 | CGTTTTCGCC | AACGTTTTTT | ATAAATCTAT | ATTTAAGTAG | CTTTATTGTT |
| 4651 | GTTTTTATGA | TTACAAAGTG | ATACACTAAC | TTTATAAAAT | TATTTGATTG |
| 4701 | GAGTTTTTTA | AATGGTGATT | TCAGAATCGA | AAAAAAGAGT | TATGATTTCT |
| 4751 | CTGACAAAAG | AGCAAGATAA | AAAATTAACA | GATATGGCGA | AACAAAAGG |
| 4801 | TTTTTCAAAA | TCTGCGGTTG | CGGCGTTAGC | TATAGAAGAA | TATGCAAGAA |
| 4851 | AGGAATCAGA | ACAAAAAAAA | TAAGCGAAAG | CTCGCGTTTT | TAGAAGGATA |
| 4901 | CGAGTTTTCG | CTACTTGTTT | TTGATAAGGT | AATTATATCA | TGGCTATTAA |
| 4951 | AAATACTAAA | GCTAGAAATT | TTGGATTTTT | ATTATATCCT | GACTCAATTC |
| 5001 | CTAATGATTG | GAAAGAAAAA | TTAGAGAGTT | TGGGCGTATC | TATGGCTGTC |
| 5051 | AGTCCTTTAC | ACGATATGGA | CGAAAAAAAA | GATAAAGATA | CATGGAATAA |
| 5101 | TAGTAATATT | ATACAAAATG | GAAAGCACTA | TAAAAAACCA | CACTATCACG |
| 5151 | TTATATATAT | TGCACGAAAT | CCTGTAACAA | TAGAAAGCGT | TAGGAACAAG |
| 5201 | ATTAAGCGAA | AATTGGGGAA | TAGTTCAGTT | GCTCATGTTG | AGATACTTGA |
| 5251 | TTATATCAAA | GGTTCATATG | AATATTTGAC | TCATGAATCA | AAGGACGCTA |
| 5301 | TTGCTAAGAA | TAAACATATA | TACGACAAAA | AAGATATTTT | GAACATTAAT |
| 5351 | GATTTTGATA | TTGACCGCTA | TATAACACTT | GATGAAAGCC | AAAAAGAGA |
| 5401 | ATTGAAGAAT | TTACTTTTAG | ATATAGTGGA | TGACTATAAT | TTGGTAAATA |
| 5451 | CAAAAGATTT | AATGGCTTTT | ATTCGCCTTA | GGGGAGCGGA | GTTTGGAATT |
| 5501 | TTAAATACGA | ATGATGTAAA | AGATATTGTT | TCAACAAACT | CTAGCGCCTT |
| 5551 | TAGATTATGG | TTTGAGGGCA | ATTATCAGTG | TGGATATAGA | GCAAGTTATG |
| 5601 | CAAAGGTTCT | TGATGCTGAA | ACGGGGAAA | TAAATGACA | AACAAAGAAA |
| 5651 | AAGAGTTATT | TGCTGAAAAT | GAGGAATTAA | AAAAGAAAT | TAAGGACTTA |
| 5701 | AAAGAGCGTA | TTGAAAGATA | CAGAGAAATG | GAAGTTGAAT | TAAGTACAAC |

Fig. 11-5

```
5751  AATAGATTTA  TTGAGAGGAG  GGATTATTGA  ATAAATAAAA  GCCCCCTGAC
5801  GAAAGTCGAA  GGGGGTTTTT  ATTTTGGTTT  GATGTTGCGA  TTAATAGCAA
5851  TACAATTGCA  ATAAACAAAA  TGATCTTCCT  TCAGGTTATG  ACCATCTGTG
5901  CCAGTTCGTA  ATGTCTGGTC  AACTTTCCGA  CTCTGAGAAA  CTTCTGGAAT
5951  CGCTAGAGAA  TTTCTGGAAT  GGGATTCAGG  AGTGGACAGA  ACGACACGGA
6001  TATATAGTGG  ATGTGTCAAA  ACGCATACCA  TTTTGAACGA  TGACCTCTAA
6051  TAATTGTTAA  TCATGTTGGT  TACGTATTTA  TTAACTTCTC  CTAGTATTAG
6101  TAATTATCAT  GGCTGTCATG  GCGCATTAAC  GGAATAAAGG  GTGTGCTTAA
6151  ATCGGGCCAT  TTTGCGTAAT  AAGAAAAAGG  ATTAATTATG  AGCGAATTGA
6201  ATTAATAATA  AGGTAATAGA  TTTACATTAG  AAAATGAAAG  GGGATTTTAT
6251  GCGTGAGAAT  GTTACAGTCT  ATCCCTGGCG  AAAGGGGGAT  GTGCTGCAAG
6301  GCGATTAAGT  TGGGTAACGC  CAGGGTTTTC  CCAGTCACGA  CGTTGTAAAA
6351  CGACGGCCAG  TGAGCGCGCG  TAATACGACT  CACTATAGGG  CGAATTGGGT
6401  ACCGGGCCCC  CCCTCGAGGT  CGACGGTATC  GATAAGCTTG  ATATCGAATT
6451  CCTGCAGCCC  GGGGGATCCA  CTAGTTCTAG  AGCGGCCGCC  ACCGCGGTGG
6501  AGCTCCAGCT  TTTGTTCCCT  TTAGTGAGGG  TTAATTGCGC  GCTTGGCGTA
6551  ATCATGGTCA  TAGCTGTTTC  CTGTGTGAAA  TTGTTATCCG  CTCACAATTC
6601  CACACAACAT  ACGAGCCGGA  AGCATAAAGT  GTAAAGCCTG  GGGTGCCTAA
6651  TGAGTGAGCT  AACTCACATT  AATTGCGTTG  CGCTCACTGC  CCGCTTTCCA
6701  GTCGGGAAAC  CTGTCGTGCC  AG
```

METHODS FOR USING A TEMPERATURE-SENSITIVE PLASMID

CROSS REFERENCE TO RELATED APPLICATIONS

This application is a divisional of U.S. patent application Ser. No. 08/302,752 filed Dec. 27, 1994, which is a National Phase Application of International Application No. PCT/FR93/00248, filed Mar. 12, 1993, which claims priority of French Patent Application No. 92 03034 filed Mar. 13, 1992, priority of each of which is hereby claimed.

FIELD OF THE INVENTION

The present invention relates to a plasmid which is usable for the genetic modification of bacteria displaying positive Gram staining, especially lactic bacteria of industrial or medical importance.

It also relates to bacteria containing such a plasmid.

Lastly, it relates to genetic modification methods employing such a plasmid, either to inactivate a gene normally present in the bacterial chromosome, or to introduce and express a gene of interest.

BACKGROUND OF THE INVENTION

Many Gram bacteria displaying positive Gram staining are subjects of study as a biological model (for example bacteria of the genus Bacillus), as a fermentation strain of industrial importance (lactic acid bacteria) or as a pathogen (for example Clostridia, Listeria, Staphylococcus, Streptococcus). Many of these strains are characterized from a physiological standpoint, but few have been studied or modified genetically. The study or modification of the strains may be facilitated by the use of vectors permitting directed or non-specific insertions into the bacterial chromosome. Delivery systems which are based on the non-replicative vectors are limited to bacteria which can be transformed with a high frequency, and those utilizing replicons which are active only under certain conditions are often limited to their host range. Thus, the construction of recombinant strains requires considerable effort, and can be applied efficaciously only to certain specific microorganisms.

The addition, loss or modification of genes can transform the role of an organism in an industrial process such as fermentation.

Biotechnology seeks to facilitate the industrial use of microorganisms. For example, lactic bacteria are used in agri-foodstuffs, predominantly for the manufacture of fermented dairy products, but also outside the milk industry for the manufacture of wine, cider, cooked meats and silage.

It is hence especially desirable to have effective means available for introducing or modifying specifically and permanently certain genes in these organisms.

At the present time, modification of the chromosome in lactic bacteria is performed via a system by transformation of a non-replicative plasmid. In a single step, it is necessary to have two low-frequency events, transformation with a plasmid and recombination in the chromosome. The probability of obtaining these two events in a single step is the product of the probabilities of each; there is hence a very small chance of obtaining the modification.

Plasmid pWV01 is a cryptic plasmid initially isolated in *Lactococcus lactis* subsp. *cremoris*; it is a broad-host-range plasmid which is replicative in both Gram-positive and Gram-negative bacteria, in particular in *E. coli, Bacillus subtilis, Lactococcus lactis,* Streptococcus and Lactobacillus. It has been characterized, and its nucleotide sequence has been published by Leenhouts et al. (1991).

In Application WO 85/03495, large fragments of this plasmid are used to construct a recombinant plasmid pGK12 marked with the gene for resistance to erythromycin and/or the gene for resistance to chloramphenicol (chloramphenicol acetyltransferase (CAT)). This plasmid pGK12 cannot be used to make integrations in the bacterial chromosome.

The non-replicative plasmids used hitherto enable this problem to be alleviated, but this system requires high degrees of transformation to permit the detection of low-frequency events such as transposition or recombination in the chromosome; now, most lactic bacteria are weakly transformable.

It would be possible to overcome all these difficulties by obtaining a temperature-sensitive replicon which could be used as a delivery vector in lactic or other bacteria.

Plasmids pE194 and pSH71 have been described as naturally temperature-sensitive, above a temperature of 51° C. (J. Bacteriol., 1990, 172, 4543–4548).

SUMMARY OF THE INVENTION

Thus, the subject of the present invention is a bacterial vector plasmid of the type containing an origin of replication which is effective in Gram+ bacteria, characterized in that it contains at least:

- a marker gene which is expressed in a bacterial host strain,
- an effective replication system which is temperature-sensitive (Ts) at and above a temperature compatible with the viability of the host strain, and in that the temperature of inhibition of replication is below or equal to approximately 37° C.

The fact that the plasmid according to the invention is non-replicative at 37° C. makes it especially suitable in the case where the bacteria have a relatively low growth temperature, or when a substantial thermal shock is not desirable. The plasmid according to the invention can be used alone, it does not have to be combined with another plasmid. The inhibition of replication by temperatures above approximately 37° C. is not strain-dependent. It possesses a broad host range and can establish itself, in particular, in the traditional strains belonging to the group comprising: Bacillus, Enterococcus, Lactobacillus, Lactococcus, Streptococcus, Listeria, Pediococcus, Staphylococcus, Clostridia, Leuconostoc, *E. coli*. Among these, the following species may be mentioned by way of example: *B. subtilis, E. faecalis, L. fermentum, L. helveticus, L. bulgaricus, L. lactis, S. pyogenes, S. thermophilus, S. sanguis, L. monocytogenes.*

The plasmid according to the invention carries at least one gene coding for a selectable marker, as well as the elements needed for its expression, such as promoter, ribosome binding site, terminator, and the like. Selectable genes are, for example, genes for resistance to antibiotics (erythromycin, chloramphenicol), or genes permitting growth on a medium lacking certain ingredients, and the like.

The marker gene is integrated in the chromosome in the case of recombination.

Replication system is understood to mean a system comprising an origin of replication as well as the protein which induces its functioning; said protein is inactivated above a temperature which inhibits the replication system.

Such a plasmid replicates normally at 28° C. in a large number of bacteria. At a temperature above approximately 35° C., the replication of this plasmid is inhibited; this temperature which inhibits replication of the plasmid is relatively low, and permits multiplication and normal growth of most bacteria, especially lactic bacteria. The temperature recommended for the effective inactivation of this plasmid is 37° C.

According to one of its aspects, the subject of the present invention is a vector plasmid, characterized in that it contains the larger Cla I fragment of plasmid pWV01, possessing at least one mutation in the Thal I-Rsa I region.

More especially, a vector plasmid displaying temperature-sensitive replication according to the invention possesses at least one mutation in the region corresponding to RepA of plasmid pWV01. The RepA protein is encoded by one of the 4 open reading frames (ORF) identified on pWV01, ORF A, and is necessary for replication.

Preferred mutations of this plasmid are located in positions 972, 977, 980 and 987 of the nucleotide sequence of pWV01.

The RepA protein encoded by the plasmid according to the invention possesses, relative to the wild-type, the modifications shown in FIG. 3, namely the replacement of:

Ser by Asn,

Asp by Asn,

Val by Ile,

Arg by Gln.

Such a plasmid constitutes a broad-host-range suicide vector of a type which is unique up to the present in the field of lactic bacteria.

In effect, it enables integration in the chromosome to be split into two steps. In the first, transformation step, the plasmid is established in the cell. In the second step, the event of integration in the chromosome is selected by raising the temperature. Bacteria which are supposedly difficult to transform may thus be modified genetically.

More especially, plasmids according to the invention contain one of the sequences shown in one of FIGS. 9, 10 and 11, or a sequence representing at least 80% homology with these sequences.

The genetic tools thus developed enable genes to be introduced into the bacterial chromosome and stabilized therein.

The application of a method employing homologous recombination is, for example, chosen.

To this end, a temperature-sensitive replicon according to the invention, which contains, in addition, at least one DNA fragment homologous with the chromosomal DNA of the bacterium which it is desired to modify, is used.

According to one of its aspects, the subject of the present invention is a method for the inactivation of a gene present in the chromosome of a bacterium, characterized in that:

a) the plasmid according to the invention is introduced into the bacterium by transformation, b) the bacterium is cultured on selective medium at a temperature below the temperature of inhibition of the origin of replication, c) the culture temperature is raised to a temperature above said temperature of inhibition, d) the surviving bacteria are recovered after several multiplication cycles, at a temperature of inhibition of plasmid replication.

Step d) enables the bacteria carrying the plasmid marker to be selected.

The chromosomal fragment cloned into the plasmid can correspond to a precise gene, which is specifically inactivated by integration of the plasmid in the chromosomal copy of the gene. In the bacterial population, only this integration site will be found.

In another embodiment, the bacterial DNA present in the plasmid may be chosen from a library of chromosomal fragments for cloning, and there will be integration at random; the integration site of the plasmid differs from one bacterium to another, and mutagenesis is thus produced.

The method may also be applied to a temperature-sensitive replicon carrying a transposon. Different transposons are available for mutagenizing the chromosome.

The Ts plasmid is employed as a carrier of one of these transposons, and is, where appropriate, modified so as to be active in *L. lactis*. Each transposon carries a marker gene (e.g.: resistance gene). By applying the protocol described above (a to c), cells which have integrated the transposon in their chromosomes are obtained. These cells are selected by means of the transposon marker. In the case of transposition, the plasmid is not integrated in the chromosome.

As a variant, the vector plasmid according to the invention also contains a mobilization locus permitting conjugation. Preferably, this mobilization locus is the ori T locus, extracted from a plasmid of a Gram-positive bacterium, and which can preferably be extracted from a Streptococcus plasmid. The vector plasmid carrying this locus can be mobilized and transferred by conjugation into non-transformable bacterial species.

The method for the inactivation of a gene in a bacterium then involves the following steps:

a) a plasmid according to the invention, carrying a mobilization locus and a fragment homologous with the chromosome and/or a transposon, is introduced into the bacterium by conjugation, b) the bacterium is cultured on selective medium at a temperature below the temperature of inhibition of the origin of replication, c) the culture temperature is raised to a temperature above said temperature of inhibition, d) the surviving bacteria are recovered after several multiplication cycles, at a temperature of inhibition of plasmid replication.

The bacteria obtained at the end of step d) have undergone a recombination or transposition event and carry the marker of the transposon or of the plasmid.

As a variant, the vector plasmid according to the invention also contains a replicon which is active in *E. coli*. The vector plasmid carrying this locus, and these [sic] derivatives, may be propagated in *E. Coli* [sic]. The constructions prepared and propagated in *E. coli* at 37° C. (by means of the second replicon) may then be transferred to lactic bacteria in which only the Ts replicon will be active.

In the methods described above, after introduction of the vector plasmid into the bacterium by transformation or conjugation in step a), the plasmid is allowed to establish itself in the bacterial population, by replication, at 28–30° C.

The selectable character is expressed in all the bacteria. When the temperature rises above 35° C., the plasmid in free form becomes incapable of replicating and is hence lost during the cell divisions. Only the bacteria for which this plasmid has become integrated by recombination in the chromosome, or for which the transposon has become integrated in the chromosome, retain and transmit the genetic information carried by the plasmid or the transposon, and enabling them to grow on selective medium. The low-frequency integration events are thus selected by recovering the bacteria which multiply at 35–37° C. on selective medium.

When the plasmid is integrated in the chromosome, it possesses excellent stability, which can be of the order of 99% after 75 generations at 37.5° C.

The scheme followed for integration of the plasmid by homologous recombination is illustrated in FIG. 6.

L. lactis strain VE 6002, containing plasmid pVE6002 according to the invention, was deposited with the national collection of the Pasteur Institute, 25–28 rue du Docteur Roux, Paris, under number I-1179.

According to another of its aspects, the subject of the invention is a method enabling a heterologous gene to be introduced into a bacterium. For its implementation, a temperature-sensitive vector plasmid as has been able to be defined above, and containing, in addition, a gene coding for a protein of interest, is used under the control of the elements needed for its expression, and which are known to a person skilled in the art. Where appropriate, this gene may be carried by the transposon. The steps described below are then followed.

a) a plasmid according to the invention is introduced into the bacterium by transformation or conjugation,
b) the bacterium is cultured on selective medium at a temperature below the temperature of inhibition of the origin of replication,
c) the culture temperature is raised to a temperature above said temperature of inhibition,
d) the surviving bacteria are recovered after several multiplication cycles, at a temperature of inhibition of plasmid replication.

Step d) enables the bacteria carrying the marker of the plasmid or of the transposon to be selected.

The subject of the invention is also bacteria containing a plasmid according to the invention, in free form or integrated in the chromosome.

Such bacteria will find, in particular, applications in the field of the agri-foodstuffs, especially the dairy or cheese-making, industry.

In some of the cases described above, it is desired to be able to remove all or part of the genetic material introduced into the bacterial chromosome by the method according to the invention.

The homologous recombination method permits two steps: the first consists in selecting the event of integration of the plasmid, the second step—which is optional—consists in excising from the chromosome the replicon and the markers which do not correspond to food standards.

Excision of the replicon: integration by homologous recombination creates duplications on both sides of the Ts plasmid (FIG. 7a). It has been shown that a replicative rolling-circle plasmid integrated in the chromosome strongly stimulates homologous recombination between the neighboring sequences. When the chromosomal fragment carried by the Ts plasmid contains a marker, the duplications created by the integration enable the replicon to be excised, leaving an inactive chromosomal gene (FIG. 7a). Experimentally, the procedure entails culturing at 28° C. the strain containing the integrated plasmid (selected previously at 37° C.). At a permissive temperature, replication resumes and stimulates recombination between the repeat sequences, leading to deletion of the replicon (FIG. 7a).

The subject of the present invention is also a vector plasmid displaying temperature-sensitive replication, possessing one or more of the features already described, and in which an internal region is duplicated. The two identical sequences are placed in such a way as to flank the region which it is desired to remove. Such a plasmid is then used in a method for the inactivation of a gene or for the introduction of a heterologous gene by recombination in the bacterial chromosome, as are described above.

At the end of step d), the surviving bacteria are cultured again at a temperature below the temperature of inhibition, for example at 28–30° C., on non-selective medium. In effect, a replicative plasmid strongly stimulates homologous recombination between the neighboring sequences. The strain containing the integrated plasmid and selected previously at 35–37° C. is cultured at a permissive temperature: plasmid replication resumes, stimulating recombination between the repeat sequences. The replicon and the markers which are incompatible with, for example, a use of this system in agri-foodstuffs are excised, with possible retention of the modified gene. Selection of the bacteria which have excised the undesirable markers is done after plating out at a non-permissive temperature. This mechanism is illustrated in FIG. 7b.

BRIEF DESCRIPTION OF THE DRAWINGS

Reference will be made to the following figures:

FIGS. 1A1–1A2 and 1B1–1B2: Kinetics of loss and analysis of the copy number of pVE6002 according to the invention and of non-Ts pVE6001. L. lactis subsp. lactis IL 1403 carrying plasmid pGK12, pVE6001 or pVE6002 are cultured at 28° C. or 37.5° C. After different culture times, samples are removed and cultured at 28° C. on selective and nonselective media. 100 colonies are subcultured from the non-selective medium on the selective medium (Em 5 μg/ml) in order to evaluate the proportion of cells containing a plasmid in the population. Extractions of total DNA are done on the cultures at 28° C. or 37.5° C., without selection, for 5 h 30 min.

FIG. 2: Hybrid plasmid of pGK12 and pVE6002. pVE6043 consists of the 994-bp Sac I-Tha I fragment of pGK12 linked to the 3384-bp Tha1-Sac1 [sic] fragment of pVE6002. pVE6044 contains the reciprocal pair, the 994-bp Sac I-Tha I fragment of pVE6002 linked to the 3384-bp Tha I-Sac I fragment of pGK12. The thin lines correspond to the pGK12 DNA; the thick dotted lines to the pVE6002 DNA.

FIG. 5: Comparison of proteins analogous to Rep of PE.194.

FIG. 6: Diagram of the method for the inactivation of a gene.

FIG. 7a: Diagram of an example of excision of the Ts replicon in two steps.

FIG. 7b: Diagram of excision of the replicon by means of plasmid duplications.

FIG. 8: Construction of plasmids pG+host5 and pG+host6 from plasmid pG+host4 (or pVE6004): plasmid pG+host5 is constructed by insertion of the Ava I-Alw N I fragment of pBR 322 (which contains the origin of replication of pBR 322) into pG+host4 linearized with Nsi I. pG+host6 is constructed by insertion of the Ava I-Eco R I fragment of pBR 322 (which contains the origin of replication of pBR 322 and the gene for resistance to ampicillin) into pG+host4 linearized with Nsi I.

FIGS. 9-1–9-3: Nucleotide sequence of pG+host4.
FIGS. 10-1–10-5: Nucleotide sequence of pG+host5.
FIGS. 11-1–11-5: Nucleotide sequence of pG+host6.

DETAILED DESCRIPTION OF THE INVENTION

The examples which follow are designed to illustrate the invention without in any way limiting its scope.

Example 1
Preparation and Characterization of a Temperature-Sensitive Vector Plasmid
MATERIALS AND METHODS The work was carried out at the Laboratoire de Génétique Microbienne, Institut de Biotechnologie [Microbial Genetics Laboratory, Biotechnology Institute], INRA, 78352 Jouy-en-Josas cedex France.
Bacterial Strains, Plasmids and Culture Conditions The plasmids and the bacterial strains used are shown in Table 1. The constructions of pVE6043 and pVE6044 are described in FIG. 2; plasmids pVE6004, pVE6006 and pVE6007 are presented in FIG. 4. pVE6004 (or pG+host4) is constructed by insertion of a 445-bp PvuII DNA fragment into the blunt-ended 3340-bp ClaI-HpaII fragment of the original Ts isolate, lacking the Cm resistance gene. The 445-bp PvuII fragment contains a multicloning site, the T7 and T3 promoters and the sites for M13–20, T7, T3 and reverse primers which permit direct sequencing from the vector. This plasmid is temperature-sensitive in all the hosts tested including *E. coli*, and must be maintained at 28° C.

*E. coli* and *Bacillus subtilis* were cultured in LB medium. *L. lactis* subsp. *lactis* (*L. lactis*) is cultured on M17 medium in which lactose has been replaced by glucose. Chloramphenicol (Cm) was used at a concentration of 5 μg/ml for *L. lactis* and *B. subtilis*, respectively, and erythromycin (Em) at a concentration of 5 μg/ml and 0.5 μg/ml, respectively. Cm, azaerythromycin and erythromycin were used at respective final concentrations of 15 μg/ml, 100 μg/ml and 150 μg/ml for *E. coli*.
Molecular Cloning, Competence and Transformation Procedure Commercial enzymes were used as directed by the suppliers. Minilysates of whole cells and of plasmid DNA were prepared as described in the literature. The induction of competence and the transformation of *E. coli* and of *B. subtilis* were performed by standard procedures (Hanahan, 1985, or Niaudet et al., 1979). *L. lactis* strains were electrotransformed as described by Langella and Chopin, 1989a, the procedure being as modified by Holo and Nes, 1989.

TABLE 1

LIST OF STRAINS AND PLASMIDS

| Strain or plasmid | Genetic markers or description | Origin or reference |
|---|---|---|
| BACTERIAL STRAINS | | |
| *L. lactis:* | | |
| IL1403 | Lacking plasmid, R− M−, 2 prophages b1285 and b1286 | Chopin et al., 1984 |
| MG1363 | Lacking plasmid | Gasson, M. J. 1983 |

TABLE 1-continued

LIST OF STRAINS AND PLASMIDS

Figure 2:
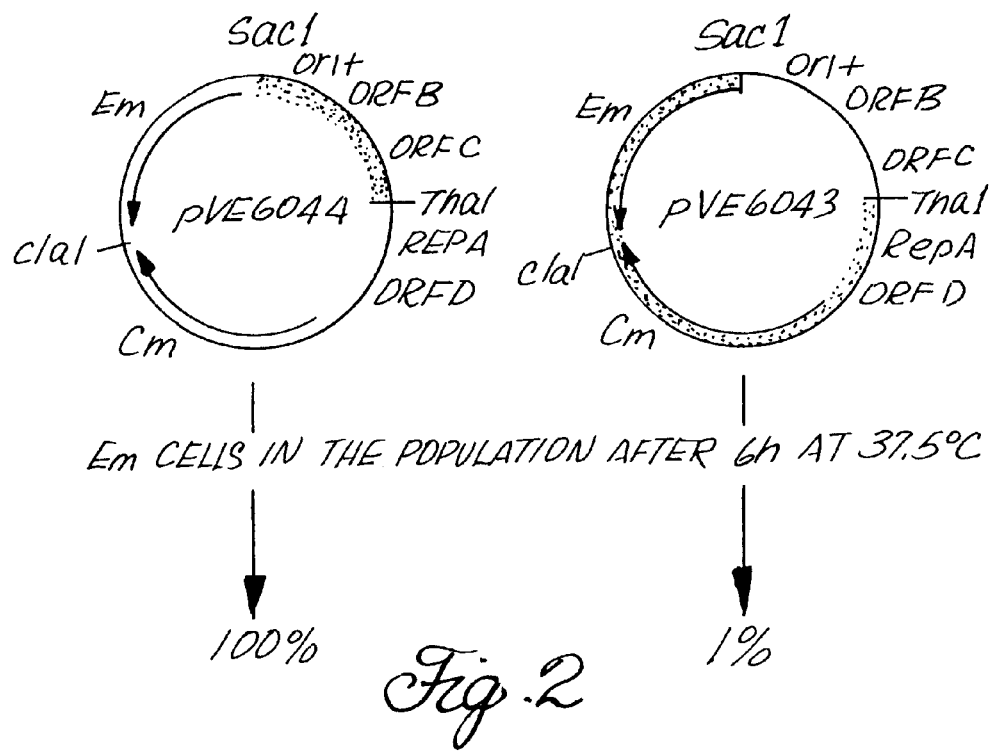
Figure 4:
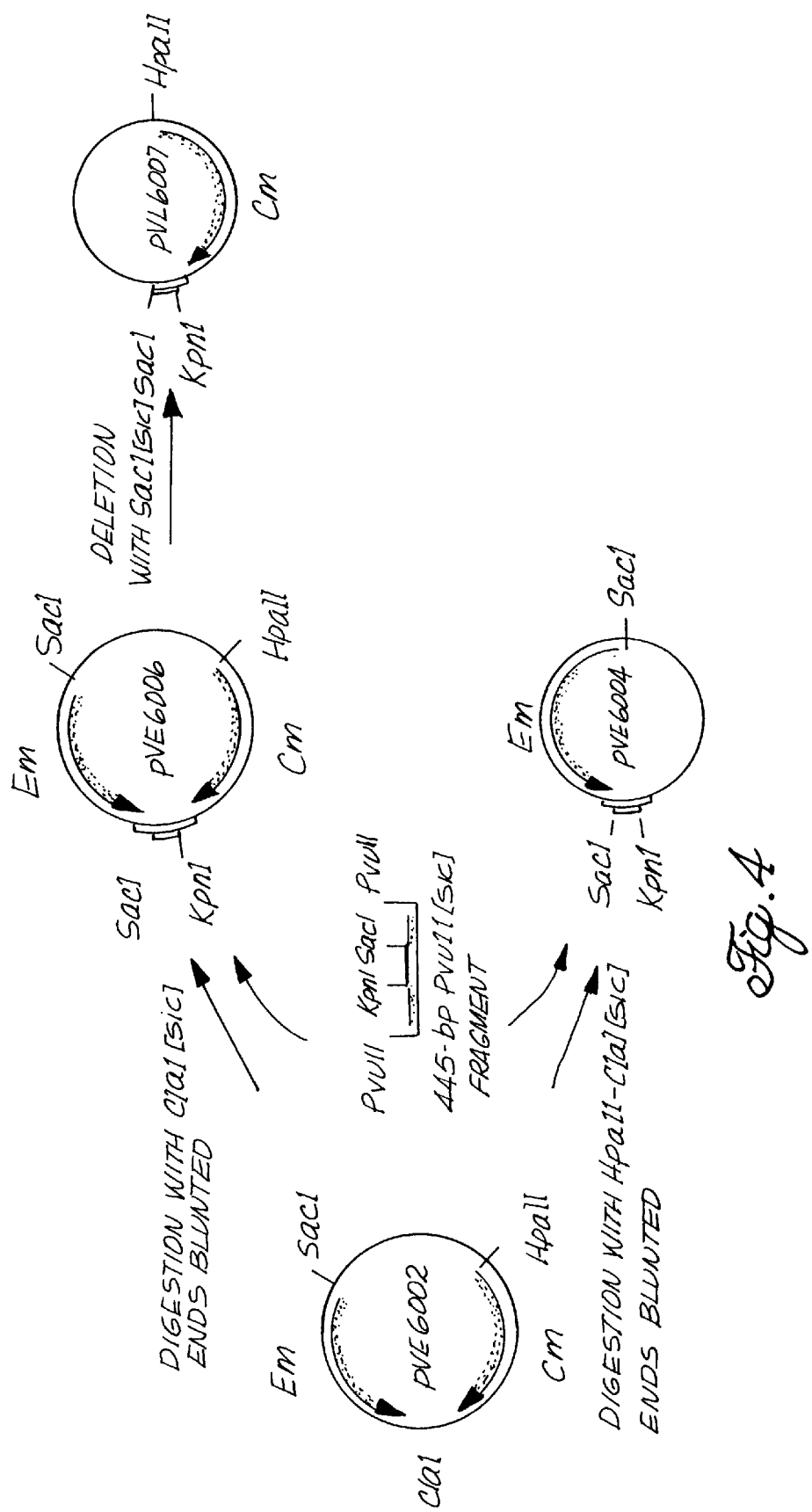
FIG. 4: Description of the temperature-sensitive derivatives. pVE6006 is constructed by insertion of the 445-bp PvuII fragment of pBluescript SK+ into the Cla I site of pVE6002. pVE6007 originates from a Sac I deletion from pVE6006, leading to loss of the gene for resistance to erythromycin. pVE6004 is constructed by insertion of the 445-bp PvuII fragment of pBluescript SK+ into the Cla I-Hpa II [sic] fragment of pVE6002 lacking the gene for resistance to chloramphenicol.

| Strain or plasmid | Genetic markers or description | Origin or reference |
|---|---|---|
| *B. subtilis:* | | |
| SB202 | trpC2, tyrAl, aroB2, hisH2, thyA | INRA laboratory |
| *E. coli:* | | |
| DH5 | F−endA1 recA1_ hsdR17 ($r_k^-$ $m_k^+$) supE44 thi1 gyrA96 re1A1 | Hanahan, D. 1985 |
| PLASMIDS | | |
| pBluescript | Ap$^r$ M13-ori pBR322-ori | Strategene |
| pGK12 | Em$^r$ Cm$^r$ | Kok et al., 1984 |
| pVE6004 | 445-bp frgt of pBluescript and 3340-bp ClaI-HpaII frgt of pVE6002 | Em$^r$ Present invention |
| pVE6006 | 445-bp frgt of pBluescript inserted into the ClaI site of pVE6002 | Em$^r$ Cm$^r$ FIG. 4 |
| pVE6007 | ScaI [sic] deletion of 1175-bp from pVE6006 | Cm$^r$ Present invention |
| pVE6043 | SstI-ThaI frgt (ori+) of pGK12 ThaI-SstI frgt (ORF A) of pVE6002 | Em$^r$ Cm$^r$ " |
| pVE6044 | SstI-ThaI frgt (ori+) of pVE6002 ThaI-SstI frgt (ORF A) of pGK12 | Em$^r$ Cm$^r$ FIG. 2 |

Mutagenesis of Plasmids

Hydroxylamine mutagenesis was performed on plasmid pGK12 DNA under the conditions described by Thomas, 1987. After 110 and 120 minutes of treatment at 70° C., the hydroxylamine is removed by isopropanol precipitation of the DNA.
DNA Sequencing For sequencing of the DNA, the Tha1 [sic] (756 bp) Rsa I (1620 bp) fragment of pVE6002 was cloned into plasmid pBluescript. A series of overlapping clones is generated by the use of exonuclease III and mung bean nuclease (Strategene). The Tha1 [sic] (756 bp)-Nde I (1140 bp) fragment of the preparation of plasmid pGK12 used for the mutagenesis is also sequenced by the same procedure.

DNA sequencing is carried out by the dideoxy chain termination method on double-stranded DNA with the Taq Dye Primer Cycle Sequencing Kit (Applied Biosystem) using a Perkin Elmer PCR apparatus. The sequencing reactions are initiated with fluorescent oligonucleotides (Applied Biosystem) and are analyzed on an automatic sequencer (370 A DNA sequencer, Applied Biosystem). The sequences obtained were determined on both strands.
RESULTS
Isolation of the Mutant The plasmid used in these experiments, pGK12, is a derivative of pWV01 containing two markers for resistance to antibiotics (KoK [sic] et al., 1984). 10 μg of plasmid DNA are mutagenized in vitro with hydroxylamine and introduced by electroporation into *lactococcus* strain IL 1403 after removal of the mutagenic agent. The efficacy of the mutagenesis is evaluated by the decrease in viability of the plasmid and by the appearance of mutants sensitive to erythromycin or to chloramphenicol. After 110 to 120 minutes of treatment, the viability of the plasmid falls to less than 0.1% and approximately 10% of the transformants contain plasmids sensitive to one of the antibiotics. These mutagenesis conditions are chosen in order to look for temperature-sensitive plasmids, identified by replication of the transformants obtained at 28° C. on a medium containing erythromycin with the transformants being incubated at 37.5° C. Two temperature-sensitive candidates, designated pVE6001 and pVE6002, are obtained by screening approximately 5000 clones. Their plasmid copy numbers are compared, and the loss at 37.5° C. is determined.

Characterization of the Mutant: pVE6001 is a Non-Ts Mutant

Plasmid pVE6001 is more unstable than pGK12 at 28° C., and this deficiency becomes more pronounced at 37.5° C. However, 7% of the bacteria still contain the plasmid after 8 hours of non-selective growth at 37.5° C., suggesting that a replication takes place under restrictive conditions (FIG. 1A, left).

Compared to pGK12, the copy number of pVE6001 is seen to be decreased at 28° C. and 37.5° C., with or without selection (FIG. 1A), which might explain its lower stability. It is possible that the loss of the plasmid at high temperatures is due to physiological changes in the host at higher temperatures, and not to the temperature sensitivity of the plasmid.

Characterization of the Mutant: pVE6002 is a Temperature-Sensitive Mutant above 35° C.

Measurements of the stability of the plasmid during growth without antibiotic reveal that pVE6002 is as stable as pGK12 at 28° C., but is lost drastically at 37.5° C. (FIG. 1B). The rapid loss of pVE6002 at 37.5° C. suggests that replication is blocked immediately after the change in temperature. After 8 hours of growth, only approximately 0.1% of erythromycin-resistant cells remain. The copy numbers of pGK12 and of pVE6002 are similar at 28° C., with and without selection; however, after 5 hours at 37.5° C., pVE6002 is undetectable, whereas the copy number of pGK12 is roughly the same (FIG. 1B). It may be concluded from these experiments that the mutation on pVE6002 genuinely constitutes a temperature-sensitive deficiency of replication.

The minimum temperature permitting the loss of pVE6002 was determined. The strain IL1403 containing pVE6002 was tested for plasmid loss during 8 hours of non-selective growth at 28° C., 30° C., 33° C., 35° C. and 37.5° C. (Table 2).

TABLE 2

| | Percentage of Em$^r$ cells in the population | | | | |
|---|---|---|---|---|---|
| | Growth temperature | | | | |
| Time (Hours) | 28° C. | 30° C. | 33° C. | 35° C. | 37.5° C. |
| 0 | 100 | 100 | 100 | 100 | 100 |
| 2 | 100 | 100 | 99 | 97 | 98 |
| 4 | 100 | 100 | 48 | 47 | 38 |
| 6 | 100 | 100 | 9 | 3 | 4 |
| 8 | 100 | 99 | 5 | 1 | 1 |

An overnight culture of IL1403 carrying pVE6002 in M17 with Em is diluted in fresh selective medium and allowed to grow for 3 hours at 28° C. The culture is then diluted 10,000 times in a non-selective medium and incubated at different temperatures. At various time intervals, samples are taken and placed on M17 at 28° C. For each temperature and time point, the loss of the plasmid is evaluated by subculturing around a hundred colonies on dishes of selective medium (Em) at 28° C.

It was found that the plasmid loss is equivalent at 37.5° C. and 35° C. Partial loss of the plasmid is already observed at 33° C., whereas the plasmid was stable at 28° C. and 30° C. Thus, cells containing pVE6002 can lose this plasmid by raising the temperature to 35° C. or more.

pVE6002 was also introduced into another strain of Lactococcus, MG1363 (Gasson, 1983), which differs from IL1403 by comparison of the pulsed-field electrophoresis profiles. Sequence analysis indicates that MG1363 is probably a L. lactis subsp. cremoris strain (Godon et al., 1992). pVE6002 shows the same temperature sensitivity in this environment, demonstrating that the phenotype of the plasmid mutant is not linked to the strain.

Broad Host Range and Ts Phenotype of pVE6002

A Ts plasmid can be a cloning vehicle which is useful in other organisms. Thus, the temperature-sensitive behavior of pVE6002 was examined in B. subtilis and E. coli. These strains were chosen as representatives of the broad host range of the original replicon pWV01. The plasmid DNA was introduced into both species by transformation and selection at 28° C. In view of the fact that B. subtilis and E. coli have maximum growth temperatures higher than those of L. lactis subsp., the replication of pVE6002 was tested at 28° C., 37° C. and 42° C. The results show that pVE6002 is temperature-sensitive in both hosts. It is probable that pVE6002 retains its temperature sensitivity properties in the broad range of hosts in which it can be established.

Mapping of the Ts Mutation

The DNA sequence of pWV01 shows the presence of an origin-plus and of four ORFs. Leenhouts deduces from its similarity with better characterized plasmid DNAs that the ORF A codes for the replication protein (RepA) responsible for the cleavage of a DNA strand at the origin-plus. Further homologies suggest that ORF C might regulate the expression of RepA. Functions have not yet been clearly assigned to ORF B and ORF D, although it is known that the latter is not needed for replication.

In order to localize the mutation which confers temperature sensitivity on pVE6002, hybrid plasmids combining portions of the temperature-sensitive replicon and unmutated portions were constructed. pVE6043 consists of a fragment of pGK12 containing the origin-plus, ORF B and ORF C, and of a pVE6002 fragment (Ts) containing ORF A (RepA) lacking its promoter, ORF D and the markers for resistance to Em and Cm (the Sac I and Tha I [sic] restriction sites are used, FIG. 2). This hybrid is lost at 37.5° C., at the same rate as pVE6002, whereas the reciprocal hybrid (pVE6044) is maintained with the same stability as pGK12 (FIG. 2). Thus, the mutation conferring temperature sensitivity on pVE6002 is located in the DNA fragment coding for RepA, ORF D and the markers for antibiotics. In view of the fact that ORF D is not essential and that the markers for antibiotics are not candidates, it may be concluded that the temperature-sensitive function is the RepA protein.

Sequencing Data

Figure 3:
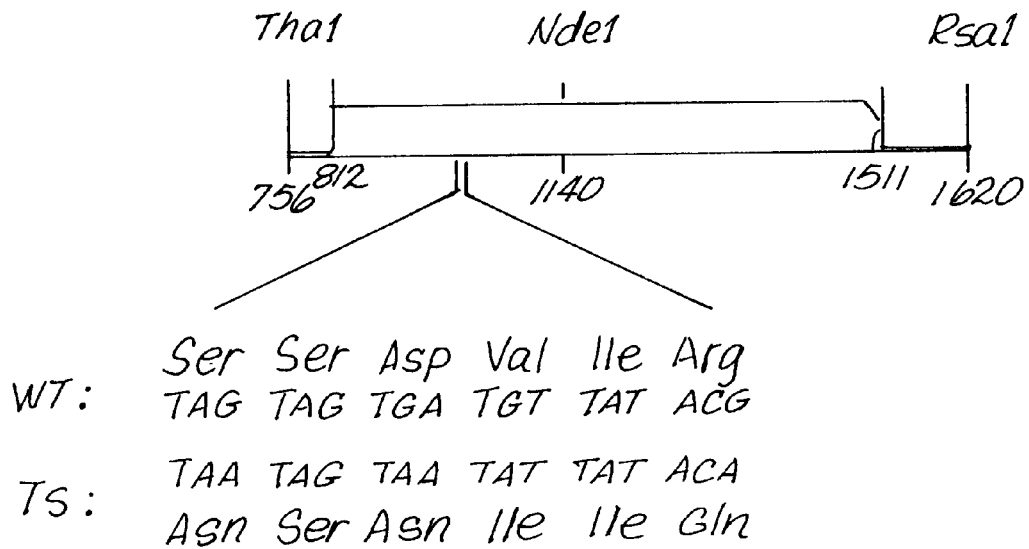
FIG. 3: Localization of the Ts mutation in the RepA gene of pVE6002. The Tha I-Rsa I fragment of pVE6002, containing the RepA gene, was sequenced on both strands. The sequence shows four mutations at positions 972, 977, 980 and 987, whereas the remainder of the sequence does not differ from the sequence published for the parent replicon pWV01.

In order to localize the Ts mutation, the 864-bp fragment coding for the RepA protein of pVE6002 was sequenced. Four mutations were identified, at positions 972, 977, 980 and 987 (FIG. 3). It was confirmed that the corresponding region of the parent plasmid pGK12 which was used for the mutagenesis is identical to the sequence published for pWV01 (Leenhouts et al., 1991). The four mutations are transitions of G to A, corresponding to the known mutagenic effect of hydroxylamine. Each change in base results in an alteration of an amino acid (FIG. 3), one of which, Val to Ile, is conservative. The contribution of one or more of these alterations may be involved in the Ts phenotype.

Derivatives of the Ts Plasmid

With the object of cloning, derivatives of the initial Ts plasmid pVE6002 were developed (FIG. 4). These derivatives are modified to contain either both antibiotic resistances (Em and Cm) or only one (Em or Cm), and they all have a multisite sequence derived from plasmid pBluescript SK+.

Excision of the Replicon

It was possible to obtain double reciprocal exchange events from a plasmid derived from pVE6002 carrying a region of homology with the bacterial chromosome interrupted by a gene for resistance to an antibiotic (Abr), as illustrated in FIG. 7a. After introduction of the plasmid into the bacterium at 28° C., a first step consists in selecting the integrants in the chromosome by culture at 37° C. on medium containing the antibiotic. The region of homology is duplicated following integration (FIG. 7a). In a second step, excision of the replicon is obtained by incubation at 28° C. in order to enable plasmid replication to resume and to stimulate a second recombination event. The excision events are selected by culture at 37° C.; the chromosomal gene is inactivated by the Abr gene.

Example 2

Integration of the Temperature-Sensitive Plasmid in the Chromosome of L. lactis

The bacterial strains and the plasmids used in this study are presented in Table 3. The *Escherichia coli* strains are cultured in LB broth. *L. lactis* is cultured and plated out on an M17⁻ glucose broth or on a minimum medium when it is tested for the ilv phenotype. Erythromycin (Em) is added at a concentration of 5 micrograms/ml for *L. lactis* subsp. *lactis* and 150 micrograms/ml for *E. coli*, and tetracycline is used at a concentration of 12.5 micrograms/ml for *L. lactis*. Electroporation of *L. lactis* subsp. *lactis* (Appl. Env. Microbiol. 55, 3119–3123, 1989) gives between $10^5$ and $10^6$ transformants per microgram of plasmid DNA for IL1403, and approximately $10^2$ transformants per microgram of plasmid DNA with NCDO2118, the ilv⁺ strain used for the gene replacement experiments. *E. coli* is transformed by the method described by Hanahan (1985, DNA cloning: A practical approach Vol 1: 109–135, IRL Press Ed Glover).

TABLE 3

| STRAIN | GENETIC MARKERS OR DESCRIPTION | SOURCE |
| --- | --- | --- |
| L. lactis: NCD02118 | natural isolate | * |
| E. coli: TG1 | supE hsdΔ5 thi Δ(lac--proAB)F[traD36pro-AB + lacI^q lacZΔ15] | Sambrook et al. |
| PLASMID | | |
| pG + host4 [sic] or pV6004 | temperature-sensitive derivative of pGK12, Em^r | ** |
| pG + host5 [sic] | NsiI frag. of pG + host4 linked to the 1.46-Kb AvaI-AlwNI fragment of pBR322 Em^r | ** |
| pVE7021 to pVE7034 | SmaI-HindIII restriction product of pG + host5 [sic] linked to a random EcoRV-HindIII fragment of the IL1403 chromosome | ** |
| pIL515 | 3.9-Kb ilv EcoRI frag. of IL1403 in pBluescript, Amp^r | ** |

TABLE 3-continued

| STRAIN | GENETIC MARKERS OR DESCRIPTION | SOURCE |
| --- | --- | --- |
| pVE7009 | 3.9-Kb EcoRI frag. of pIL515 linked to pG + host5 [sic] cut with EcoRI | ** |
| pVE7009R | same construction as pVE7009, inserted in the opposite orientation | ** |
| pVE7015 | SphI-EcoRV deletion from pVE7009R leaving a 3362-bp ilv frag. | ** |
| pVE7014 | StyI-EcoRV deletion from pVE7009R leaving a 2904-bp ilv frag. | ** |
| pVE7010 | ClaI deletion from pVE7009R leaving a 2552-bp ilv frag. | ** |
| pVE7016 | XcmI-EcoRV deletion from pVE7009R leaving a 1912-bp ilv frag. | ** |
| pVE7013 | AatII-EcoRV deletion from pVE7009R leaving a 1206-bp ilv frag. | ** |
| pVE7011 | HindIII deletion from pVE7009R leaving a 497-bp ilv frag. | ** |
| pVE7012 | PstI deletion from pVE7009R leaving a 356-bp ilv frag. | ** |
| pVE7017 | Pf1MI-EcoRV deletion from pVE7009R leaving a 330-bp ilv frag. | ** |
| pIL500 | 18.5-Kb ilv XbaI frag. of NDCO2118 chromosome in pIL253 | Godon et al. |
| pIL1202 | XbaI frag. of pG + host4 [sic] containing the 1.1-Kb XbaI-BglII and 2.5-Kb EcoRI-XbaI ends of the 18.5-Kb frag. of pIL500 linked to the 4-Kb BamHI frag. of the Tet M gene | |
| pIL1261 | 2.3-Kb XbaI-EcoRI frag. of pIL500 interrupted by a Tet M gene, 4-Kb BamHI inserted at the BglII site and linked to pBluescript XbaI-EcoRI | |
| pIL1263 | pG + host4 [sic] XbaI-EcoRI linked to the 6.3-Kb XbaI-EcoRI frag. of pIL1261 | |

*: National Collection of Dairy Organisms
**: Present invention

Construction of Plasmids for Integration a) Construction of the Vector

Plasmid pG⁺host4 (or pVE6004) is a Ts derivative of pWV01 prepared according to Example 1. To facilitate cloning in *E. coli*, the 1.4-Kb fragment containing the origin of pBR322 is inserted into pG⁺host4. Plasmid pG⁺host5 is constructed by insertion of the Ava I-Alw N I fragment of pBR 322 (which contains the origin of replication of pBR 322) into linearized pG⁺host4 cut with Nsi I. Its structure is shown in FIG. 8. The plasmid obtained, referred to as pG⁺host5 (Appligène, Illkirch, France) is used for all the clonings. The activity of the origin of pBR322 permits its maintenance at 37° C. in *E. coli*, and the Ts origin maintains pG⁺host5 at 28° C. in Gram-positive bacteria.

b) Cloning of Random Chromosomal Fragments into pG⁺host5

Chromosomal DNA of the strain IL1403 is digested with EcoRV and HindIII. Chromosomal fragments between 0.9 Kb and 1.4 Kb in size are purified from agarose gels and linked with pG⁺host5 treated with SmaI-HindIII. The recombinant plasmids are established in *E. coli*, and then introduced into *L. lactis* by electroporation. The latter organism is used to verify the structures of the plasmids and the sizes of the inserts. The results are presented in Table 4 below. The restriction enzymes Hpa1 [sic] (single site in the vector portion) and HindIII (single site between the insert and the vector) are used to analyze the integrants.

TABLE 4

Ipc at different localizations on the L. lactis chromosome

| Size of the plasmid insert | (Kb) | IPC mean ± SD |
|---|---|---|
| Group I: | | |
| pVE7025 | 1.29 | $3.0 \pm 0.3 \times 10^{-2}$ |
| pVE7034 | 1.05 | $3.8 \pm 0.5 \times 10^{-3}$ |
| pVE7021 | 1.29 | $3.4 \pm 2.6 \times 10^{-3}$ |
| pVE7024 | 0.96 | $2.5 \pm 1.3 \times 10^{-3}$ |
| pVE7030 | 1.42 | $2.3 \pm 0.8 \times 10^{-3}$ |
| pVE7028 | 1.46 | $7.2 \pm 0.7 \times 10^{-4}$ |
| pVE7023 | 1.29 | $6.6 \pm 3.9 \times 10^{-4}$ |
| pVE7022 | 1.08 | $5.7 \pm 0.3 \times 10^{-4}$ |
| pVE7027 | 1.05 | $5.2 \pm 1.3 \times 10^{-4}$ |
| pVE7026 | 0.96 | $4.0 \pm 0.5 \times 10^{-4}$ |
| Group II: | | |
| pVE7029 | 1.02 | $1.1 \pm 0.4 \times 10^{-5}$ |
| pVE7031 | 0.96 | $9.9 \pm 3.9 \times 10^{-6}$ |
| pVE7032 | 1.37 | $8.6 \pm 5.0 \times 10^{-7}$ |
| pVE7033 | 1.25 | $3.9 \pm 0.9 \times 10^{-7}$ | ipc: Frequency of integrations per cell c) Cloning and Deletion of an ilv Operon Fragment A 3949-bp EcoRI fragment of the ilv operon of IL1403 (J. Bacteriol 174, 6580–6589 (1992) [lacuna] is cloned in either orientation at the Eco RI site of pG+host5 (to give pVE7009 and pVE7009R).

Integration by Single Crossing-Over (sco) in the L. lactis Chromosome

Lactococcus strains containing the test plasmids are cultured overnight at 28° C. in the presence of erythromycin, then diluted 100 times in the same medium and cultured at 28° C. for 2 hours to 2½ hours (exponential phase). The cultures are placed at 37.5° C. for 3 hours in order to decrease the number of copies of plasmids per cell. The samples are then diluted and plated out at 37° C. on M17 Em medium in order to detect the integration events, and at 28° C. on non-selective medium to determine the number of viable cells. The frequency of integration per cell (ipc) is estimated as the ratio of $Em^r$ cells at 37° C. to the number of viable cells at 28° C. The integrants isolated at 37° C. are maintained in an M17 medium containing Em at 37.5° C. for subsequent use.

Integration by Double Crossing-Over (dco) in the L. lactis Chromosome

Plasmids pIL1263 and pIL1202 are composed of the Ts vector (pG+host4, $Em^r$) and, respectively, the 2.3-Kb or 3.6-Kb chromosomal regions interrupted by the Tet gene of Tn1545 (Nucl. Acids Res., 14, 7047–7058, 1986). A strain carrying pIL1202 or pIL1263 is cultured overnight at 37.5° C. in M17 with Tet or Em to obtain a population of integrants. The culture is then diluted to $1/10^5$ in M17 medium without antibiotic, and brought to 28° C. in order to stimulate recombination by plasmid replication. Culturing for 12 hours or more at 28° C. gives maximum gene replacement frequencies. An overnight culture at 28° C. is plated out at different cell concentrations at 37° C. with or without selection by Tet. Colonies in which gene replacement has taken place have a $Tet^r$ and Em-sensitive ($Em^s$) phenotype. Chromosomal DNA is prepared according to known methods (Grüss et al., 1988).

The purified DNA is treated with restriction enzymes, separated by agarose gel electrophoresis and analyzed by Southern hybridization with DNA probes to detect homologous recombinations (Sambrook et al., 1989).

Results

1) Integration by Single Crossing-Over

The cloning of chromosomal fragments of L. lactis into pG+host5 in E. coli enables 14 different plasmids each containing a different chromosomal insertion, from 0.9 Kb to 1.4 Kb, to be isolated. These plasmids established in IL1403 at 28° C. are used to measure the frequencies of integration in the L. lactis chromosome. The frequency of integration per cell is between $10^{-2}$ and $10^{-7}$. The ipc of a pG+host5 vector without chromosomal insert is between $10^{-6}$ and $10^{-7}$. Plasmids carrying the chromosomal inserts may be classified in two groups in accordance with their frequency of integration. In group I, the ipc varies between $3 \times 10^{-2}$ and $4 \times 10^{-4}$. These variations must be due to the localization or the nature of the insert rather than to its size. In group II, the ipc of the plasmid is between $10^{-5}$ and $3 \times 10^{-7}$. This is probably due to the interruption of an essential chromosomal gene, which enables only non-homologous integrations to be observed. Only two of these plasmids (pVE7028 and pVE7034) produce high molecular weight (HMW) molecules. Analysis of the chromosomal DNA obtained from the integrant strains maintained at 37° C., by enzymatic restriction and Southern hybridization using plasmid pG+host5 as probe, indicates a single and multi-tandem integration in the case of eight plasmids and an integration by multiple copies in the case of two plasmids. Digestion of the DNA of the integrants with HindIII confirms that the integration takes place by single crossing-over. Each plasmid contains only one HindIII site at the vector-insert junction, and digestion should liberate a single band of plasmid-sized DNA. Southern hybridization of the undigested total DNA does not reveal a free plasmid in any of the group I plasmids, indicating that the copy of the plasmid is integrated. A similar analysis of plasmids pVE7028 and pVE7034 confirms that these plasmids are also integrated by single crossing-over. The use of HpaI, which recognizes a single site within the vector, enables it to be determined that each plasmid is integrated at a different position.

The four group II plasmids (low frequency of integration) appear to be integrated at random, since HindIII digestion does not liberate a monomeric band of plasmid, and HpaI digestion of three integrants of the same plasmid does not give the same profile on gel. The restriction map of the L. lactis chromosome developed for SmaI and ApaI enables the integration sites of the plasmids by single crossing-over to be localized on the chromosome map. Each integrant is present on a different segment. These results collectively indicate that the chromosomal insertions are positioned randomly on the chromosome, thus ruling out any bias in the procedure.

The frequency of integration depends on the length of homology.

A 3.9-Kb segment of the ilv operon of IL1493 which is sequenced is cloned into pG+host5, and a set of deletions from the fragment is generated on the same vector. Whereas plasmids carrying the total insert of 3.9 Kb in one of the two orientations (pVE7009 and pVE7009R) possess some degree of structural instability in L. lactis, the eight deletion derivatives of pVE7009R are stable. These clones are used to study the relationship between the length of homology and the frequency of integration. A logarithmic relationship exists between the frequency of integration and the length of homology for lengths between 0.35 and 2.5 Kb. For fragments over 2.5 Kb, the frequencies of recombination appear to reach a plateau, since the ipc values of homologous segments of 2.5, 3.3 and 3.9 Kb are not significantly different. Factors other than length are also seen to be important. Analysis with restriction enzymes which recognize a single site, either in the vector or in the insert or in the vector-insert junction, confirms that the integration takes place by homologous recombination by single crossing-over. For each plasmid used, multicopy integrations of the plasmid take place. These results show that pG+host provides an effective means of integration by single crossing-over if it carries homologous segments as small as 330 base pairs.

2) Integration by Double Crossing-Over

In the single crossing-over (sco) system described above, the integrated plasmid is flanked by repeat sequences. Thus, when the integrant strains generated at 37° C. are placed at 28° C., replication of the plasmid strongly stimulates a second recombination event. The consequence of this event is a high frequency of excision of the replicon, leading either to the parent structure or to the dco (double crossing-over) chromosomal structure.

A weakly transformable strain of L. lactis, NCDO2118, which is prototrophic for the branched amino acids (Ilv, Leu, Val) and in which no genetic modification could be carried out hitherto, is used. Two derivatives of pG+host4 which carry either an adjoining or a non-adjoining chromosomal segment are used. pIL1263 contains a 2.3-Kb chromosomal fragment upstream of the ilv operon, interrupted by a 4-Kb DNA segment containing a marker for resistance to tetracycline (Tet$^r$). Substitution of the gene should lead to insertion of the Tet$^r$ marker into the chromosome and leave the ilv$^+$ operon intact. Plasmid pIL1202 contains non-adjoining 1.1-Kb and 2.5-Kb segments, corresponding to the ends of an 18.5-Kb region, including the ilv operon, joined via the 4-Kb Tet$^r$ marker. Replacement of the gene should lead to a deletion from the chromosome of 14.9 Kb including the ilv operon and giving an ilv$^-$ phenotype.

Selection of the Replacement Gene

A strain containing either pIL1202 or pIL1263 is cultured under conditions described above, using Tet as selectable marker. In independent experiments with pIL1263, 69% and 98% of Tet$^r$ colonies were Em$^s$; with pIL1202, 50% and 91% of Tet$^r$ colonies are Em$^s$. In control cultures maintained at 37° C. for the same period, all the Tet$^r$ colonies are also Em$^r$. This result indicates that replication in rc plasmids (displaying circular replication) stimulates excision from the chromosome. Five Em$^s$ colonies obtained by integration of pIL1202 are cultured on minimum medium lacking branched amino acids and are ilv$^-$, thereby confirming that recombination has taken place. The structure of the corresponding chromosomal region of five Tet$^r$ Em$^s$ isolates is studied by Southern hybridization, which confirms the replacement of the gene in all the cases.

No Selection

An identical protocol was used without selection by Tet, so as to deal with the case where the chromosomal fragment carried by the plasmid does not have a selectable marker. In three experiments using pIL1263 (gene insertion), 10% to 40% of the colonies obtained at 37° C. without selection are Tet$^r$ Em$^s$, indicating that a gene replacement event has taken place. For pIL1202 (chromosome deletion), 1% to 7% of colonies are Tet$^r$ Em$^s$, indicating a replacement of the gene; of the four Tet$^r$ Em$^s$ colonies tested, all are ilv$^-$. Analysis of the chromosomal structure of the four dco integrants of each type confirms that replacement takes place without selection of a new inserted fragment. These results demonstrate the feasibility of gene replacement without leaving an antibiotic marker in the chromosome. This protocol is hence suited to chromosomal modification without the use of selectable markers.

Use of pG+host in Other Gram-Positive Bacteria

The efficiency of intermolecular recombination in twelve different localizations of the B. subtilis chromosome was determined by transforming competent cells with a non-replicative plasmid (J. Bacteriol. 174, 5593–5587, 1992). In these experiments, the homologous segment is invariant (insertion of a fragment of pBR322). The efficiencies vary approximately threefold in accordance with the position of integration. Using the sco pG+host system instead of the non-replicative vector, experiments of identical recombination may be performed on the two B. subtilis strains with differences of an order of three in the frequencies of integration. pG+host5 carrying the 1.4-Kb fragment of pBR322 is introduced into the B. subtilis strains of interest. Using the sco procedure described above, the frequency of integration varies between $1.8 \pm 0.6 \times 10^{-3}$ and $6.1 \pm 0.9 \times 10^{-4}$. The same threefold variations are observed between the two different localizations as those obtained with the non-replicative system. This result demonstrates the efficiency of the system.

Example 3

Genetic Modification of Non-Transformable Organisms

Organisms of industrial importance such as some lactobacilli are not at present transformable; it is, however, possible to introduce plasmids into them by conjugation. The mobilization locus oriT of plasmid pIP501 has been characterized. pIP501 is autotransferrable into some of these lactobacilli.

This oriT fragment was cloned into the Ts plasmid (plasmid Ts:oriT); its capacity to be mobilized in the presence of a helper plasmid (derived from pIP501), which provides the proteins for transfer in trans, was tested. Several intra- or inter-species crosses were carried out successfully (Table 5); with exconjugants which contain only plasmid Ts:oriT, the future method of integration by recombination is applicable. It is hence possible to introduce genetic information into the chromosome of Lactobacillus bulgaricus, a non-transformable species used increasingly by the dairy industry.

The objective of the method of integration by recombination is modification of the genetic characters of bacterial strains; this assumes that the properties to be modified are characterized at molecular level. The development of a functional transposition system (combination of the Ts plasmid of a transposon would represent a considerable contribution as a genetic tool for the analysis of L. lactis.

TABLE 5

FREQUENCY OF CONJUGATION WITH PLASMID TS:oriT

| Recipient | Donor L. lactis IL1403/pHelper/pTs:oriT |
|---|---|
| L. lactis IL1403 str$^r$ | $5 \times 10^{-3}$ exc/don* |
| E. faecalis IL1885 str$^r$ | $10^{-5}$ exc/don |
| L. bulgaricus IL1687 str$^r$ | $3 \times 10^{-5}$ exc/don |
| S. sanguis IL1474 str$^r$ | $3 \times 10^{-7}$ exc/don |

*exc/don: Number of exconjugants containing Ts:oriT per donor cell

Example 4
Use of a Temperature-Sensitive Plasmid as Vector for a Transposon A transposition cassette Tn10 cloned into a derivative of pVE6004 is used for a transposition test. Approximately 1% of the cells are Em$^r$ at 37° C., indicating that the transposon or the plasmid is integrated in the chromosome. Non-specific integration of the plasmid without the transposition cassette takes place at frequencies of less than $10^{-7}$. Transposition is estimated by analysis of the DNA digested with HindIII from eight colonies. HindIII has two restriction sites in the plasmid but none in the transposable unit. The chromosomal DNA is extracted from eight Em$^r$ thermo-resistant clones and digested with HindIII; the treated DNA is then separated by agarose gel electrophoresis and hybridized with a DNA fragment containing the Em$^r$ transposon as probe. Under these conditions, integration of the whole vector (that is to say without transposition) would lead to a hybridization band of 1.3 Kb, which is not observed here. Each chromosomal sample gives a single profile when the DNA fragment containing the transposon is used as probe. None of the hybridized bands has a size of 1.3 Kb, which would be expected if the whole plasmid were integrated in a site of the vector. In addition, hybridization is not observed when the Ts vector plasmid is used as probe. These results indicate that transposition takes place at different sites, and that the plasmid DNA does not integrate in the chromosome with the transposon. The temperature-sensitive plasmid may hence be used as a delivery vector.

LEGEND TO THE FIGURES
FIG. 4
Single Sites
AccI KpnI
BamHI NotI
BstXI PstI
DraII SalI
EagI SacII
EcoRI SmaI
EcoRV SpeI
HindIII XbaI
XhoI FIG. 6
Symbols
☐▨☐: Active chromosomal gene
▨: Region of homology between the plasmid and the chromosome
Ab$^r$: Resistance to an antibiotic
⋅⋅: Recombination event FIG. 7A
Symbols
☐▨ ▨☐: Active chromosomal gene
▨ ▨: Regions of homology between the plasmid and the chromosome
Tet$^r$: Resistance to tetracycline (Other markers may be used)
Em$^r$: Resistance to erythromycin
⋅⋅: Recombination event

LEGEND TO THE FIGURES
FIG. 7B
Symbols
☐▨☐: Active chromosomal gene
▨: Region of homology between the plasmid and the chromosome
→: Plasmid duplication
Ab$^r$: Resistance to an antibiotic
⋅⋅: Recombination event

REFERENCES

Chopin, A., M C. Chopin, A. Moillo-Batt, and P. Langella. 1984. Plasmid II: 260–263.

Gasson, M. J. 1983, J. Bacteriol. 154: 1–9.

Godon, J-J., C., Delorme, P., Renault and S. D. Ehrlich. 1992. Appl. Env. Microbiol. submitted.

Godon, J J., M C. Chopin and S. D. Ehrlich. 1992. J. Bacteriol. 174: 6580–6589.

Grüss, A., and S. D. Ehrlich. 1988. J. Bacteriol, 170: 1183–1190

Hanahan, D. 1985. In DNA cloning: A practical approach Vol. 1: 109–135. IRL Press Ed Glover.

Holo, H., and Nes, I, F. 1989. Appl. Env. Microbiol. 55: 3119–3123.

Kok. J., J. M. B. van der Vossen and G. Venema. 1984. Appl. Env. Microbiol. 48: 726–731.

Langella, P., and Chopin, A. 1989. FEMS Microbiol. Lett. 89: 301–306.

Leenhouts, K., J., B., Tolner, S., Bron, J., Kok, G., Venema and J., F. M. L. Seegers. 1991. Plasmid. 26: 55–66.

Niaudet, B; Ehrlich, S, D. 1979. Plasmid 2: 48–58.

Petit, M A., Mesas, M., J., Noirot, P., and Ehrlich, S., D. 1992. Inducible Amplification in the Bacterial Chromosome. submitted.

Sambrook J., F Fritsh, and T., E. Maniatis. 1989. Molecular cloning: a laboratory manual. Cold Spring Harbor Laboratory, Cold Spring Harbor, N.Y.

Thomas C. M. 1987. In Plasmids. A practical approach, IRL Press EDS Hardy.

We claim:

1. A method for inactivating a gene in bacteria, comprising:
   a) introducing into the bacteria a bacterial vector plasmid which comprises
      i) an origin of replication which is effective in Gram-positive bacteria other than Streptomyces,
      ii) a marker gene which is expressed in a bacterial host strain,
      iii) an effective replication system which is temperature sensitive at and above a temperature compatible with the viability of the host strain and wherein replication is inhibited at a temperature of below or equal to 37° C.;
   b) culturing the bacteria on a selective medium at a temperature equal to or below the temperature of inhibition to form a culture,
   c) raising the temperature of the culture to a temperature above the temperature of inhibition, and
   d) recovering the surviving bacteria after several multiplication cycles, wherein the bacterial chromosomal DNA sequence is interrupted by integration of the marker gene.

2. A method for introducing a heterologous gene into bacteria, comprising:
   a) introducing into the bacteria a bacterial vector plasmid which comprises
      i) an origin of replication which is effective in Gram-positive bacteria other than Streptomyces,
      ii) a marker gene which is expressed in a bacterial host strain,
      iii) an effective replication system which is temperature sensitive at and above a temperature compatible with the viability of the host strain and wherein replication is inhibited at a temperature of below or equal to 37° C., and iv) the heterologous gene;

b) culturing the bacteria on a selective medium at a temperature below or equal to the temperature of inhibition to form a culture, c) raising the temperature of the culture to a temperature above the temperature of inhibition, and d) recovering the surviving bacteria after several multiplication cycles, wherein the heterologous gene has been integrated into the chromosomal DNA of the bacteria.

3. A method according to claim 1 or 2, further comprising again culturing, on a non-selective medium, the recovered surviving bacteria at a temperature below the temperature of inhibition of the origin of replication.

4. A method according to claim 1 or 2, wherein the bacteria are cultured on a selective medium at a temperature of approximately 28° C.

5. A method according to claim 1 or 2, wherein the plasmid further comprises a replication system which is effective in lactis bacteria.

6. A method according to claim 1 or 2, wherein the plasmid further comprises at least one DNA sequence homologous with chromosomal DNA sequence, so as to permit recombination.

7. A method according to claim 6, wherein the marker gene is located so as to be integrated in the chromosomal DNA sequence during recombination.

8. A method according to claim 1 or 2, wherein the marker gene provides for resistance to a chemical compound or is a gene permitting complementation of an auxotrophy.

9. A method according to claim 1 or 2, wherein the temperature-sensitive-replication is inhibited above approximately 35° C.

10. A method according to claim 1 or 2, wherein the plasmid comprises a mobilization locus permitting conjugation.

11. A method according to claim 10, wherein the mobilization locus of the plasmid is an ori T locus of a plasmid of a Gram-positive bacterium.

12. A method according to claim 10, wherein the plasmid further comprises a replicon which is active in *E. coli*, making the plasmid a Gram-negative, Gram-positive shuttle plasmid.

13. A method according to claim 1 or 2, wherein the plasmid comprises two identical repeat sequences flanking a sequence of the plasmid.

14. A method according to claim 1 or 2, wherein the replication system is carried by the larger ClaI fragment of plasmid pWV01, possessing at least one mutation in the ThaI-RsaI region.

15. A method according to claim 14, wherein the plasmid comprises at least one mutation in the region corresponding to Rep A of plasmid pWW01.

16. A method according to claim 14, wherein the plasmid comprises at least one mutation in at least one of positions 972, 977, 980, and 987 of PWV01.

17. A method according to claim 14, wherein the replication system of the plasmid codes for a protein possessing mutations shown in FIG. 3.

18. A method according to claim 14, wherein the plasmid is replicative at 28° C. and non-replicative at a temperature above 35° C.

19. A method according to claim 1 or 2, wherein the plasmid comprises a transposon.

20. A method according to claim 1 or 2, wherein the heterologous gene codes for a protein of interest, wherein said gene is under control of elements needed for its expression.

21. A method according to claim 1 or 2, wherein the bacterial vector plasmid is introduced into the bacteria by transformation or conjugation.

* * * * *

UNITED STATES PATENT AND TRADEMARK OFFICE
CERTIFICATE OF CORRECTION

PATENT NO. : 5,919,678
DATED : July 6, 1999
INVENTOR(S) : Alexandra Gruss; Emmanuelle Maguin Column 3,
Line 37, after "and 11" insert -- (SEQ ID NO. 1, SEQ ID NO. 2, and SEQ ID NO. 3, respectively) --.

Column 4,
Lines 44, 45, delete "[sic]" (both occurrences).

Column 6,
Line 32, delete "[sic]".

Column 7,
Lines 4-7, delete lines 4-7 and insert therefor
-- FIG. 9: Nucleotide sequence of pG+host 4 (SEQ ID NO. 1).
FIG. 10: Nucleotide sequence of pG+host 4 (SEQ ID NO. 2).
FIG. 11: Nucleotide sequence of pG+host 6 (SEQ ID NO. 3). --.

Column 8,
Line 12, that portion under Genetic markers or description
"F⁻end A1 recA1_hsdR17 ($r_k^- m_k^+$)" should read
-- F⁻endA1 recA1 hsdR17 ($r_k^- m_k^+$) --.
Line 24, after ScaI" delete "[sic]".
Lines 41, 45, delete "[sic]" (both occurrences).

Column 10,
Line 59, replace "confirmed" with -- configured --.

Column 11,
Line 23, replace "Abr" with -- $Ab^r$ --.
Line 53, that portion under Genetic markers or description
"Ab + lacl$^q$lacZΔ15]" should read -- Ab + lacl$^q$lacZΔM15] --.

UNITED STATES PATENT AND TRADEMARK OFFICE
CERTIFICATE OF CORRECTION

PATENT NO. : 5,919,678
DATED : July 6, 1999
INVENTOR(S) : Alexandra Gruss; Emmanuelle Maguin It is certified that error appears in the above-identified patent and that said Letters Patent is hereby corrected as shown below:

Column 12,
Line 17, replace "XcmI-EcoRV" with -- ScmI-EcoRV --.

Column 20,
Line 31, replace "claim 1 or 2" with -- claim 2 --.

Signed and Sealed this

Twenty-first Day of August, 2001

*Attest:*

*Attesting Officer*

NICHOLAS P. GODICI
*Acting Director of the United States Patent and Trademark Office*